US010835381B2

(12) United States Patent
Linder-Ganz et al.

(10) Patent No.: US 10,835,381 B2
(45) Date of Patent: Nov. 17, 2020

(54) TWO-PIECE FLOATING JOINT REPLACEMENT DEVICE WITH A RIGID BACKING MATERIAL

(71) Applicant: Active Implants LLC, Memphis, TN (US)

(72) Inventors: Eran Linder-Ganz, Tel Aviv (IL); Jonathan J. Elsner, Cambridge, MA (US); Henry A. Klyce, San Francisco, CA (US)

(73) Assignee: Active Implants LLC, Memphis, TN (US)

( * ) Notice: Subject to any disclaimer, the term of this patent is extended or adjusted under 35 U.S.C. 154(b) by 56 days.

(21) Appl. No.: 16/047,759

(22) Filed: Jul. 27, 2018

(65) Prior Publication Data

US 2019/0029835 A1 Jan. 31, 2019

Related U.S. Application Data

(60) Provisional application No. 62/538,059, filed on Jul. 28, 2017.

(51) Int. Cl.
*A61F 2/38* (2006.01)
*A61F 2/30* (2006.01)

(52) U.S. Cl.
CPC ........ *A61F 2/3872* (2013.01); *A61F 2/30767* (2013.01); *A61F 2/3868* (2013.01);
(Continued)

(58) Field of Classification Search
CPC .................. A61F 2/3868; A61F 2/3872; A61F 2002/3895; A61F 2002/30754
See application file for complete search history.

(56) References Cited

U.S. PATENT DOCUMENTS 4,207,627 A 6/1980 Cloutier
5,358,531 A * 10/1994 Goodfellow .......... A61F 2/3868
623/20.29
(Continued)

FOREIGN PATENT DOCUMENTS

EP 1327424 A1 7/2003

OTHER PUBLICATIONS

International Search Report and Written Opinion received in Patent Cooperation Treaty Application No. PCT/US2018/044196, dated Oct. 17, 2016, 17 pages.
(Continued)

*Primary Examiner* — Brian A Dukert
*Assistant Examiner* — Amanda M Barkan
(74) *Attorney, Agent, or Firm* — Haynes and Boone, LLP

(57) ABSTRACT

A two-part joint replacement device for replacing damaged soft joint tissue, such as a meniscus or cartilage tissue. In one form, the device may include a free floating soft joint tissue replacement component comprising a first tissue-interface surface shaped to engage a first anatomical (bone and/or cartilage) structure of a joint having damaged soft tissue. The device may also include a free floating rigid base component comprising a second tissue-interface surface shaped to engage a second anatomical (bone and/or cartilage) structure of the joint. The free floating soft joint tissue replacement component may be shaped to slidably interface with the rigid base component. In another form, the free floating soft joint tissue replacement component and the rigid base component are fixed together.

22 Claims, 16 Drawing Sheets

(52) U.S. Cl.
CPC . *A61F 2/30965* (2013.01); *A61F 2002/30014* (2013.01); *A61F 2002/30065* (2013.01); *A61F 2002/30133* (2013.01); *A61F 2002/30187* (2013.01); *A61F 2002/30754* (2013.01); *A61F 2002/3895* (2013.01); *A61F 2210/0071* (2013.01)

(56) References Cited

U.S. PATENT DOCUMENTS

| | | | |
|---|---|---|---|
| 5,871,543 A * | 2/1999 | Hofmann | A61F 2/3868 623/20.32 |
| 5,879,387 A | 3/1999 | Jones et al. | |
| 5,964,808 A | 10/1999 | Blaha et al. | |
| 6,206,927 B1 | 3/2001 | Fell et al. | |
| 7,291,169 B2 | 11/2007 | Hodorek | |
| 2003/0055500 A1 * | 3/2003 | Fell | A61F 2/38 623/14.12 |
| 2003/0114934 A1 | 6/2003 | Steinberg | |
| 2003/0187510 A1 * | 10/2003 | Hyde | A61B 17/68 623/18.12 |
| 2004/0199249 A1 * | 10/2004 | Fell | A61F 2/38 623/14.12 |
| 2004/0247541 A1 | 12/2004 | Felt et al. | |
| 2005/0209703 A1 * | 9/2005 | Fell | A61F 2/38 623/20.33 |
| 2005/0278025 A1 | 12/2005 | Ku et al. | |
| 2007/0067032 A1 | 3/2007 | Felt et al. | |
| 2007/0293947 A1 | 12/2007 | Mansmann | |
| 2009/0259314 A1 * | 10/2009 | Linder-Ganz | A61F 2/4684 623/14.12 |
| 2012/0209396 A1 | 8/2012 | Myung et al. | |
| 2014/0135938 A1 | 5/2014 | Assell et al. | |

OTHER PUBLICATIONS

Australian Patent Office, Examination Report, for Application No. 2018306750, dated May 15, 2020, 4 pages.

* cited by examiner

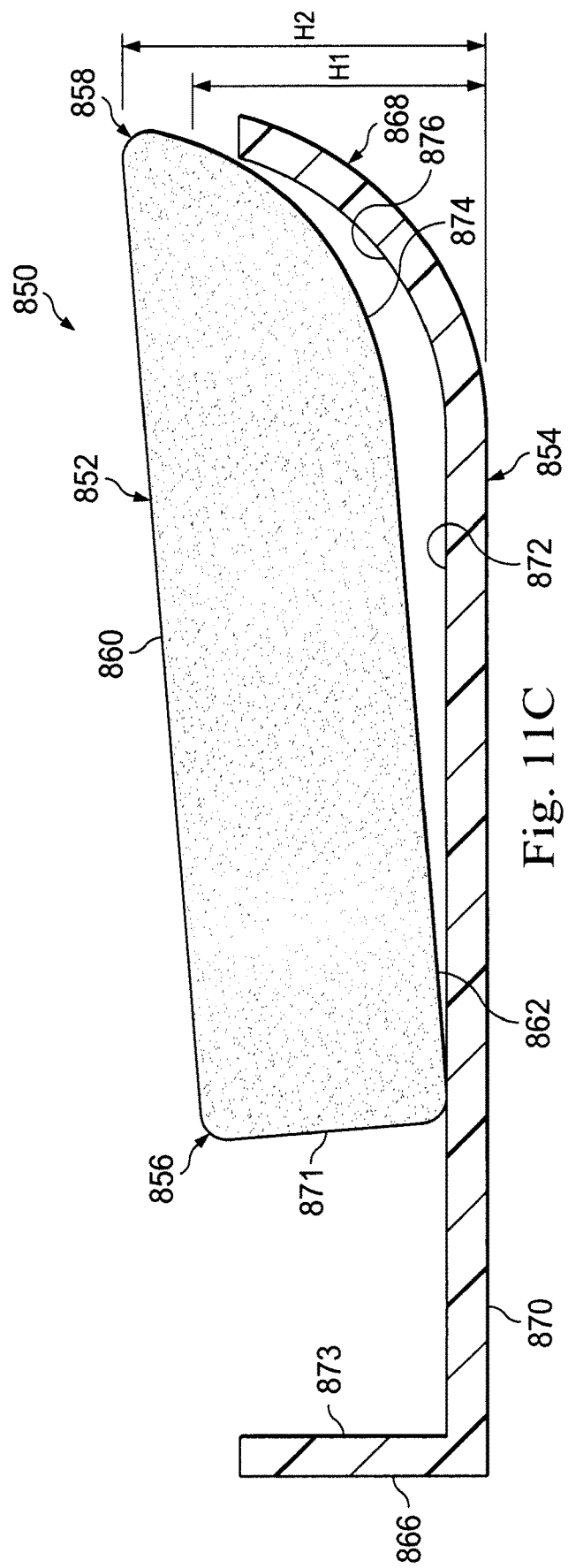

TWO-PIECE FLOATING JOINT REPLACEMENT DEVICE WITH A RIGID BACKING MATERIAL

PRIORITY DATA

This application claims priority to U.S. Provisional Patent Application Ser. No. 62/538,059, filed on Jul. 28, 2017, the entire disclosure of which is hereby incorporated herein by reference.

FIELD OF THE INVENTION

The disclosure generally relates to medical prosthetic devices and methods. More specifically, the disclosure relates to prosthetic devices that replace at least part of the functionality of the natural soft tissue, such as a meniscus or cartilage, at joint bearing surfaces.

BACKGROUND

A knee has two menisci, a lateral meniscus and a medial meniscus. Each meniscus is a crescent-shaped fibrocartilaginous tissue attached to the tibia at an anterior and a posterior horn. Damage to the meniscus can cause pain and arthritis. Further, damage to cartilage on the bearing surfaces of the tibia and femur may lead to additional pain and may cause additional damage to the meniscus. Accordingly, current practices for treating patients with damaged knee cartilage are to perform a total knee replacement. Alternatively, if the damaged cartilage is limited to one side of the knee, a unicompartmental knee replacement procedure may be performed where the femur and tibia bones are milled off and implants are inserted into both bones to perform the bearing function of the knee. In such a procedure, even though cartilage of only one of the bone surfaces is damaged, both cartilage surfaces will be removed and replaced with an artificial bearing surface. The total or unicompartmental knee replacement procedures are invasive and result in significant pain and rehabilitation time for the patient.

There remains a need for less traumatic and bone sparing devices that can accomplish load bearing and joint function through a range of joint motions. While existing devices, systems, and methods have attempted to address these issues, they have not been satisfactory in all respects. Accordingly, there is a need for the improved devices and methods described herein in accordance with the disclosure.

SUMMARY

This disclosure is directed to prosthetic joint replacement devices designed to replace damaged soft tissue in bone joints, such as, for example, a knee joint, a shoulder joint, or other joint. In some aspects, the prosthetic devices disclosed herein may be used to replace tissue such as a meniscus or cartilage that may be found between adjacent anatomical (bone and/or cartilage) structures in a joint.

In an example aspect, the present disclosure is directed to a two-part joint replacement device for replacing a damaged soft joint tissue. The device may include a free floating soft joint tissue replacement component comprising a first tissue-interface surface shaped to engage a first anatomical (bone and/or cartilage) structure of a joint having damaged soft tissue. The device may also include a free floating rigid base component comprising a second tissue-interface surface shaped to engage a second anatomical (bone and/or cartilage) structure of the joint. The free floating soft joint tissue replacement component may be shaped to slidably interface with the rigid base component. In another aspect, one or both of the free floating soft joint tissue replacement component and the rigid base may include external passages, including loops, for the passage of suture like materials to loosely connect the devices to surrounding tissue while still allowing free floating movement in the joint space.

In another example aspect, the present disclosure is directed to a method for inserting a two-part joint replacement device inside a joint between a first anatomical structure and an adjacent second anatomical structure. The method may include introducing a free floating soft joint tissue replacement component and a rigid base component between the first anatomical structure and the second anatomical structure of the joint so that the free floating soft joint tissue replacement component is disposed to slidingly engage inside the rigid base component. The upper surface of the free floating soft joint tissue replacement component may be positioned to engage the first anatomical structure. A bottom portion of the rigid base component may be positioned to engage the second anatomical structure such that the two-part joint replacement device floats between the first and second anatomical structures.

In another example aspect, the present disclosure is directed to a two-part floating soft joint tissue replacement prosthetic device for replacing damaged soft tissue, such as a meniscus or cartilage, of a joint. The device may include a free floating first soft joint tissue replacement component comprising a first surface for engagement with first anatomical structure having damaged soft joint tissue, the first soft joint tissue replacement component being formed of a first biocompatible material. The device may also include a rigid base component as a second component fixed with the first soft joint tissue replacement component and comprising a bottom portion arranged to provide free floating engagement with a second anatomical structure. The rigid base component may be formed of a second biocompatible material more rigid than the first biocompatible material and disposed for direct engagement with anatomical tissue. In another aspect, the free floating soft joint tissue replacement device may include external passages, including loops, for the passage of suture like materials to loosely connect the device to surrounding tissue while still allowing free floating movement in the joint space.

BRIEF DESCRIPTION OF DRAWINGS

Other features and advantages of the disclosure will become apparent in the following detailed description of embodiments of the disclosure with reference to the accompanying of drawings.

FIGS. 11A, 11B, and 11C are diagrammatic cross-sectional side views of a prosthetic meniscus device, according to an exemplary implementation.

DETAILED DESCRIPTION

Figure 1:
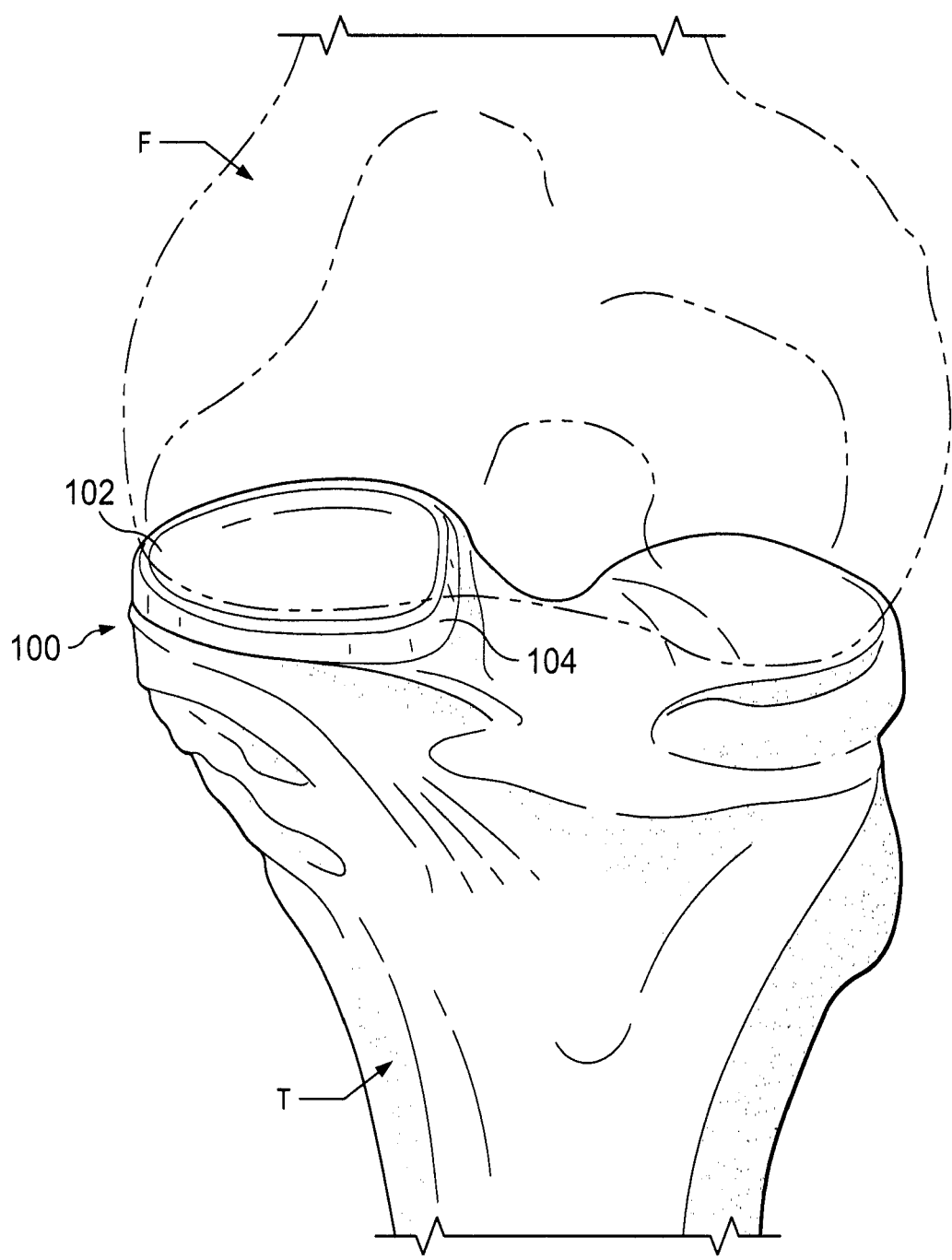
FIG. 1 is a diagrammatic view of a prosthetic meniscus device implanted in a left knee joint between femur F and tibia T, according to an exemplary implementation.

For the purposes of promoting an understanding of the principles of the disclosure, reference will now be made to the embodiments illustrated in the drawings, and specific language will be used to describe the illustrated embodiments. It is nevertheless understood that no limitation of the scope of the disclosure is intended. Any and all alterations or modifications to the described devices, instruments, and/or methods, as well as any further application of the principles of the disclosure that would be apparent to one skilled in the art are encompassed by the disclosure even if not explicitly discussed herein. Further, it is fully contemplated that the features, components, and/or steps described with respect to one embodiment may be combined with the features, components, and/or steps described with respect to other embodiments of the disclosure.

FIG. 1 is a diagrammatic view of a two-part prosthetic meniscus device 100 (also referred to as a joint replacement device) implanted in a joint. The prosthetic meniscus device 100 may be used to replace tissue such as a meniscus or cartilage that may be found between adjacent anatomical (bone and/or tissue) structures in a joint. As used herein, bone structure on adjacent sides of a joint is typically not considered to be soft-tissue. In the example shown, the joint is a left knee joint and the prosthetic meniscus device 100 is disposed between femur F and tibia T. In this example, the prosthetic meniscus device 100 is implanted into the knee such that the prosthetic meniscus device floats inside the knee joint. As used herein, the term "float" means that the device is not anchored in the joint using a mechanical device structure, such as a screw, a fin, a pointed protrusion, or other structure that would penetrate the bone or soft tissue like the joint capsule to secure the device in place. Because the prosthetic meniscus device 100 floats inside the knee joint, the implant may not cause, or may at least minimize, permanent damage to the patient's undamaged tibia or other bone and/or soft tissue structure(s) engaged by the prosthetic meniscus device 100 in some embodiments. In some instances, the prosthetic meniscus device 100 is implanted to alleviate the patient's knee problems while avoiding permanent destruction of the patient's anatomy, which may occur if traditional joint repair techniques are used, such as cutting or reaming a large opening in the tibia or anchoring the prosthetic meniscus device 100 to the soft tissue. Because the surrounding bone structure may remain largely or completely intact, in some instances, the prosthetic meniscus device 100 may be subsequently removed and replaced with another prosthetic device or treatment without adversely affecting the subsequent treatment. While the prosthetic meniscus device 100 will be described herein primarily with reference to a knee joint meniscus device that may be disposed between a femur and tibia, other implementations of the prosthetic meniscus device are suitably shaped and sized for implantation in a shoulder joint, an ankle joint, a hip joint, or other joint in the human body.

In some implementations, the prosthetic meniscus device 100 replaces some or all of the function of a natural meniscus and is configured to interact with the opposing articulating cartilage surfaces to facilitate movement of a joint with a damaged meniscus. In the example of a knee joint, the prosthetic meniscus device 100 device may be disposed between tibia and femur surfaces to facilitate movement of a knee joint having a damaged meniscus. In some implementations, the prosthetic meniscus device 100 is inserted between tibia and femur surfaces of a knee joint and prevents further deterioration of the medial meniscus and articulating cartilage surfaces. In another embodiment, prosthetic meniscus device 100 serves as a temporary implant that is in place while natural meniscus is treated or regrown with a biologic. In that regard, the prosthetic meniscus device 100 can be disposed between and in contact with a lateral femoral bearing surface or medial femoral condyle in the femur and the natural lateral tibial plateau in the tibia. In a further embodiment, the prosthetic meniscus device 100 mimics the function of the natural meniscus and redistributes weight load transmitted across the knee joint, as well as protect the articulating cartilages.

As illustrated in FIG. 1, prosthetic meniscus device 100 has been inserted into the medial compartment of the native tibial plateau, according to an embodiment. Unlike conventional implants, prosthetic meniscus device 100 is not fixed to the bone or soft tissues of the knee joint. Instead, prosthetic meniscus device 100 floats inside the medial compartment between the femoral bearing surface and the native tibial plateau, and engages the femoral bearing surface and the native tibial plateau when the knee is in motion.

In an embodiment, the prosthetic meniscus device 100 includes a free floating meniscus component 102 (also referred to as a soft joint tissue replacement component) and a free floating rigid base component 104. The free floating meniscus component 102 has a circular or a semi-elliptical body. The free floating meniscus component 102 is a component of prosthetic meniscus device 100 that redistributes weight load transmitted across the knee joint while protecting the cartilage of the medial femoral condyle and protect/delay from further damage to the meniscus implant by the native tibial plateau. In an embodiment, the free floating meniscus component 102 is made of polycarbonate-urethane (PCU), a similar medical grade plastic, or a combination of one or more plastics of same or different densities. Example plastics are described in detail below. These plastics allow the free floating meniscus component 102 to conform and fit the natural components of the knee joint, and also adapt to the changes of the natural components of the knee joint with time and use.

In the illustrated embodiment, the free floating meniscus component 102 is placed inside the rigid base component 104, such that the free floating meniscus component 102 is surrounded by the rigid base component 104 along its outer portion and bottom surface area. The rigid base component 104 is placed inside the native tibial plateau of the medial compartment and prevents the free floating meniscus component 102 from being expelled from the medial compartment, when, for example, the knee is in motion. Importantly, the rigid base component 104 is not fixed or attached to the native tibial plateau and is also free floating inside the medial compartment. Like the free floating meniscus component 102, rigid base component 104 can also be made of polycarbonate-urethane (PCU) or another similar medical grade plastic which may be of different density/stiffness from the free floating meniscus component 102. Typically, the rigid base component 104 is made up of plastic that is denser than the free floating meniscus component 102. In another embodiment, rigid base component 104 may be made of a bio-compatible, non-reactive metal, such stainless steel, cobalt chrome, or titanium, to name a few examples. In yet another embodiment, the rigid base component 104 may be made of a bio-compatible ceramic material.

In other embodiments (not illustrated here), prosthetic meniscus device 100 may also be utilized in other joints about the body. In addition, it may be used in any of the other knee bearing surfaces and menisci, such as the right knee medial meniscus, left knee lateral meniscus, and/or right knee lateral meniscus. In that regard, the size, shape, thickness, material properties, and/or other properties of the prosthetic meniscus device 100 may be configured for each particular application, and also to the size and shape of the knee, knee joints, shoulder, hip, ankle, compromised and non-compromised menisci, etc., of each patient.

Figure 2:
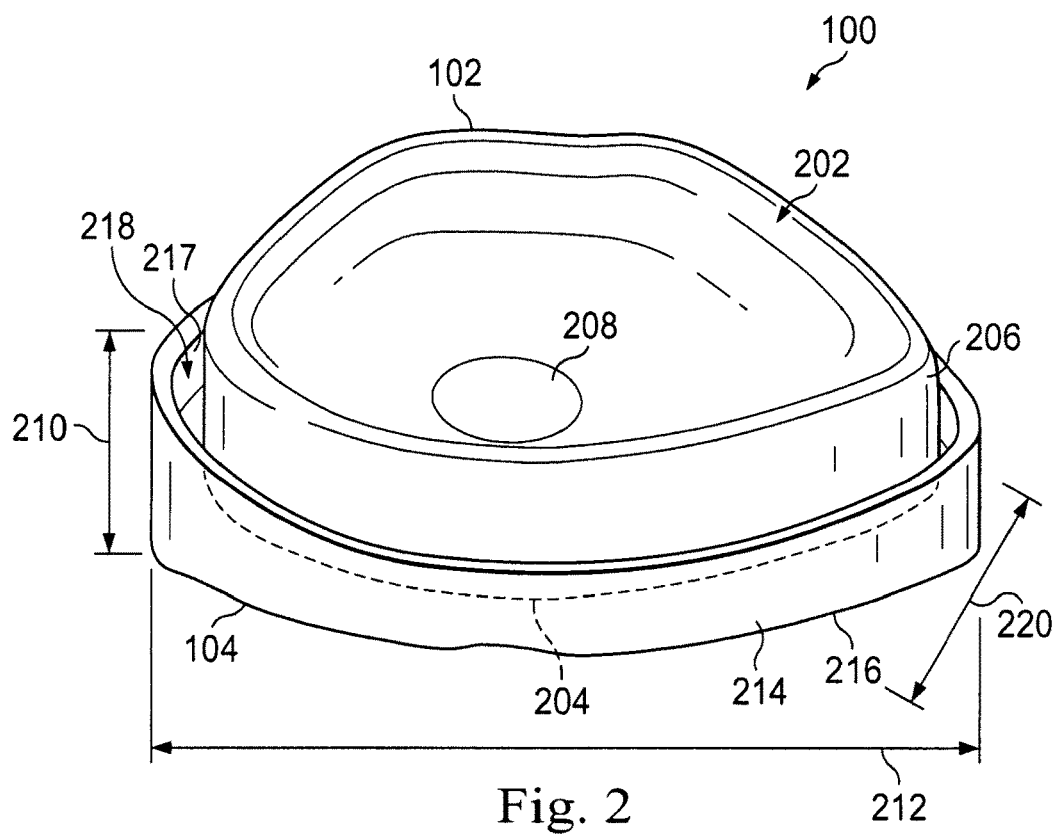
FIG. 2 is a diagrammatic perspective view of a prosthetic meniscus device, according to an exemplary implementation.

FIG. 2 is a perspective view of the two-part prosthetic meniscus device 100, according to an exemplary implementation. Referring to FIG. 2, the free floating meniscus component 102 comprises a tissue-interfacing upper surface 202, a lower surface 204 (also shown in FIG. 7) and an outer portion 206. In some implementations, the outer portion 206 forms the outer peripheral surface of the component 102 that extends between and connects the sides of the upper surface 202 and the lower surface 204. In some implementations, the outer portion 206 is formed as a monolithic part of the component 102, and in some implementations, the outer portion 206 is formed of a wall structure or peripheral bumper formed or molded about the central portions forming the upper surface 202 and the lower surface 204 of the free floating meniscus component 102. In some implementations, such as when the free floating meniscus component 102 is formed of two elements joined together, the peripheral wall structure or wall may have a circular or elliptical shape that surrounds and may be attached to the body of the free floating meniscus component 102. The outer portion 206 may also comprise of a denser/stiffer material than the rest of the free floating meniscus component 102.

In the illustrated embodiment, the upper surface 202 is shaped and arranged to face the medial femoral condyle and may press or engage the cartilage of the medial femoral condyle or the femoral surface. In some embodiments, the upper surface 202 may be custom molded to shape the cartilage of the medial femoral condyle of the host knee.

In some implementations, upper surface 202 may be shaped to form a basin or have a generally concave shape for the reception of adjacent bone structure forming the joint. In some implementations, the upper surface 202 may have one or more bone-relief recess areas, such as bone-relief recess area 208. Bone-relief recess area 208 is an indentation in the upper surface 202 of the free floating meniscus component 102. The bone relief recess area 208 may be manufactured by any method including molding, machining, etching, or other method. The bone-relief recess area 208 limits contact or engagement between the upper surface 202 and the bone structure otherwise supported within the basin or concave shape of the upper surface 202. For example, when the joint is a knee, the bone-relief recess area 208 may limit contact or engagement between the upper surface 202 and a portion of the medial femoral condyle that is opposite of the bone-relief recess area 208, while the upper surface 202 still supports other portions of the medial femoral condyle. The bone-relief recess area 208 may be shaped as an additional divot, depression, or etch formed in the upper surface 202.

Such limited contact between the upper surface 202 and a portion of the adjacent bone may be provided for medical reasons, for general comfort, or for other reasons. For example, when certain areas of the meniscus in the bone structure at the treated joint have been damaged, further contact with prosthetic meniscus device 100 would exacerbate the damage or cause additional pain to the patient. In this case, when the free floating meniscus component 102 with the bone-relief recess area 208 is inserted into the medial compartment such that the bone-relief recess area 208 faces the damaged portion of the femoral bearing surface, the bone-relief recess area 208 may limit contact with the damaged surface and prevents further deterioration of the femoral bearing surface, while the remainder of upper surface 202 still provides supportive contact with the non-damaged cartilage portions the bone structure.

In another example, limited contact between the prosthetic meniscus device 100 and the femoral bearing surface may be necessitated after a patient underwent a minimally invasive surgery to replace or repair a portion of the cartilage of the medial femoral condyle. One way to replace or repair portions of the cartilage is to insert a biologic or stem cell paste into the damaged portions or the cartilage and allow the cartilage to regenerate and regrow. However, cartilage does not regenerate at a density required to bear weight in the knee joint unless pressure is applied to the cartilage. Hence, in order for the cartilage to regenerate at a necessary density, a patient should apply pressure on the knee and on the femoral bearing as the cartilage regenerates and regrows. In order for the patient to put pressure on the knee, yet for the biologic or the stem cell paste to have limited or no contact with the prosthetic meniscus device 100, the upper surface 202 includes the bone-relief recess area 208 that faces the portion of the medial femoral condyle that has been injected with a biologic or stem cell paste. The bone-relief recess area 208 may prevent or may limit contact between the prosthetic meniscus device 100 and the portion of the medial femoral condyle that was injected with a biologic or the stem cell paste while the cartilage regenerates. Yet, at the same time, bone-relief recess area 208 also allows a patient to apply pressure to the knee that causes the cartilage to regenerate at a density that supports pressure on a knee joint.

In some implementations, rigid base component 104 comprises an outer portion 214 and a bottom portion 216. Generally, the outer portion 214 is a rigid support structure or wall that forms an outer periphery of the base component 104 and has a circular or an elliptical shape that imitates or substantially matches the shape of the outer portion 206 of the free floating meniscus component 102. The bottom portion 216 is also of a circular or elliptical shape and attaches to the lower end of the outer portion 214 on all sides. In some implementations, this outer portion 214 and the bottom portion 216 together form a basin or cup in which the free floating meniscus component 102 may be disposed. In some implementations, the surface areas of an inner surface and an outer surface of the outer portion 214 may be smooth surfaces.

In some implementations, bottom portion 216 may be molded to conform to the shape of the lower surface 204 and/or the shape of the natural medial tibial plateau of the host knee. The bottom portion 216 may include a lower surface or tissue-interfacing surface that interfaces with the bone/cartilage tissues of the joint.

In the illustrated embodiment, the free floating meniscus component 102 is disposed inside the rigid base component 104, such that the lower surface 204 of the free floating meniscus component 102 faces the upper surface of the bottom portion 216 of the rigid base component 104. Here, the lower surface 204 and the upper surface of the bottom portion 216 directly interface. In an embodiment, lower surface 204 may be a smooth surface that is adjacent to the smooth surface of the bottom portion 216. In another embodiment, lower surface 204 may be a molded surface, in which case, the upper surface of the bottom portion 216 is molded to the shape of lower surface 204 or vice versa. In yet another embodiment, lower surface 204 may be a concave surface and the upper surface of the bottom portion 216 may also be a concave surface. In additional embodiments, they are each planar.

Referring to FIG. 2, when the free floating meniscus component 102 is located inside the rigid base component 104, the outer portion 214 and the bottom portion 216 surround the free floating meniscus component 102. Accordingly, the bottom portion 216 provides a load bearing surface through which loads on the joint may be passed, and the outer portion 214 may be a boundary or limit upon the distance that the free floating meniscus component 102 may translate as it free floats within the rigid base component 104. In the illustrated embodiment, the upper surface 202 and upper portions of the outer portion 206 protrude above the outer portion 214 of rigid base component 104. This may provide axial separation of the upper bone structure from the lower component of the device 100, which in this example is the rigid base component 104.

FIG. 2 shows that the prosthetic meniscus device 100 has a height or thickness 210, a longitudinal width 212 that may be measured along the largest transverse cross-sectional length, and a transverse width 220 that is the smallest cross-sectional length taken perpendicular to the longitudinal width 212. The thickness or height 210 may be measured as the combined height of the free floating meniscus component 102 and the rigid base component 104. Also, the thickness or height 210 may vary depending upon the measured location. For example, the nonplanar upper surface 202 of the free floating meniscus component 102 and the nonplanar lower surface 308 of the rigid base component 104 may impact the thickness or height 210 at any particular location of the prosthetic meniscus device 100. Generally, in addition to the surface variations and shapes of the upper surface 202, the thickness or height 210 may be selected to fit within the available space between the femoral bearing surface and the natural tibial plateau of a host knee. In some implementations, the thickness or height 210 may be between 0.5 mm and 15 mm. In some implementations, maximum height 210 measured along the outer edges of the may be about 10 mm and the minimum thickness or height 210, which may be measured in the central portion of the prosthetic meniscus device 100 may be about 2 mm. Other thicknesses or heights, both smaller and larger are contemplated.

In some implementations, the longitudinal width 212 of prosthetic meniscus device 100 may be the width of rigid base component 104 since the width of the rigid base component will generally be larger than the width of the free floating meniscus component 102. Generally, the longitudinal width 212 may be dictated by the available space between the medial femoral bearing surface and the natural medial tibial plateau of a host knee. The longitudinal width 212 may be between 25 mm and 70 mm, although larger and smaller widths are contemplated.

In some implementations, the transverse width 220 of the prosthetic meniscus device 100 may be the shortest measurable width of the rigid base component 104 that is perpendicular to the longitudinal width 212. Generally, the transverse width 220, like the longitudinal width 212, may be dictated by the available space between the femoral surface and the natural medial tibial plateau of a host knee. The transverse width may be between 20 mm and 50 mm in some implementations, although larger and smaller transverse widths are contemplated.

In some implementations, the inner dimensions of the outer portion 206 may be larger than the outer dimensions of the free floating meniscus component 102 so as to provide a gap or space 218 therebetween. The space 218 provides clearance between the outer portion 206 and the free floating meniscus component 102 so that the free floating meniscus component 102 may laterally translate or rotate while disposed in the outer portion 206. The inner surface of the outer portion 206 may act as a boundary to limit the amount of translation and to maintain the free floating meniscus component 102 within the outer portion 206. The size of the gap or space 218 may vary depending on the application and the joint to be replaced. In some implementations, the space 218 may be between 0.5 mm and 3 mm, but the implementation is not limited to this embodiment. In a different embodiment, the space may so small such that the outer portion 214 and inner surface of the outer portion 206 may be substantially abutting around the complete outer portion to limit translation in any direction.

In some implementations, the wall formed by the outer portion 206 of the rigid base component 104 prevents free floating meniscus component 102 from being expelled from the joint. At the same time, the rigid base component 104 allows free floating meniscus component 102 to float freely therein, and the prosthetic meniscus device 100 may mimic functionality of the natural meniscus. Further, because the rigid base component 104 also floats within the joint, the natural meniscus and the supporting femur and tibia may remain intact. That is, since tissue penetrating anchors are not employed in some embodiments of the prosthetic meniscus device 100, additional trauma to the joint may be reduced or minimized when compared to conventional devices.

Figure 3:
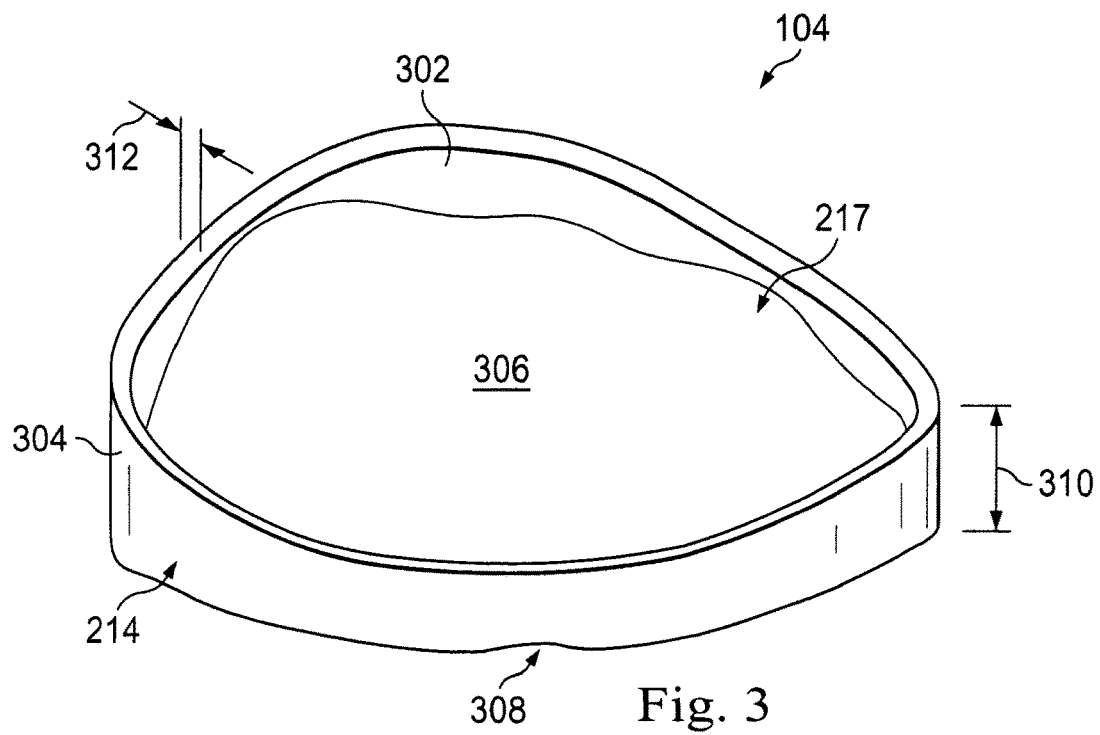
FIG. 3 is a diagrammatic perspective view of a rigid base component of a prosthetic meniscus device according to an exemplary implementation.

FIG. 3 is a perspective view of the rigid base component 104 of the prosthetic meniscus device 100, according to an example implementation. The rigid base component 104 may be formed of a rigid, supportive material such as a metal, a plastic, and/or a ceramic material. As illustrated in FIG. 3, the outer portion 214 and the bottom portion 216 together form a basin or cup defining a containment cavity 217 that is shaped to receive the free floating meniscus component 102 (FIG. 2). The outer portion 214 forms the peripheral wall of rigid base component 104 and comprises an inner surface 302 and an outer surface 304. The inner surface 302 of the rigid base component 104 faces the outer portion 206 of the free floating meniscus component 102 when the free floating meniscus component 102 is disposed therein. In some embodiments, inner surface 302 may be a smooth surface and may be arranged to provide a limit or restraint on the distance that the free floating meniscus component 102 may translate in the containment cavity 217.

In some implementations, the outer surface 304 of rigid base component 104 may be shaped to be positioned inside the boundaries of the joint, such as, for example, within a medial compartment of the knee. This may permit the outer surface 304 to be surrounded by the meniscus in the native tibial plateau. In some implementations, the rigid base component 104 may be positioned within boundaries of the joint, such as the native tibial plateau such that the bottom portion 216 is adjacent and conforms to the shape of the meniscus inside the native tibial plateau.

In some implementations, the bottom portion 216 of rigid base component 104 comprises the upper surface 306 and the lower surface 308. As shown in FIG. 3, the upper surface 306 of the bottom portion 216 may be molded to have a non-planar, uneven surface that may be arranged to match the lower surface 204 of the free floating meniscus component 102. In some implementations, the lower surface 308 of the bottom portion 216 may be molded to fit the underlying bone structure against which it abuts. For example, when the rigid base component 104 is a knee implant, the lower surface 308 may be molded to fit a natural tibial plateau and/or the meniscus surrounding the native tibial plateau, such that the native tibial plateau and the meniscus provide support for keeping the rigid base component 104 in place. Since the lower surface 308 abuts directly against and interfaces with bone and/or cartilage structures, such a form-fit surface may help maintain the free floating rigid base component 104 in place, even though free floating displacement may be expected. That is, variations in the height or thickness of the surfaces may be selected to match the anatomical features of the patient in some embodiments in the form of a natural meniscus.

In some implementations, the thickness or height 310 of the outer portion 214 or wall may vary between a maximum height or thickness in the range of 10 mm to 20 mm and may vary between a minimum height of 2 mm to 10 mm depending upon the location and/or the size of the patient. Height variations may be due to the preformed shape of the bottom portion 216 to coincide with the lower surface 204 of the free floating meniscus component 102 and/or with the shaped of the adjacent bone/cartilage structure, such as the native tibial plateau. In some implementations, the height 310 of outer portion 214 varies from a maximum height of 20 mm to a minimum height of 10 mm. In other implementations, the height 310 varies from a height of 15 mm to a height of 5 mm. Other amounts are also contemplated. In some implementations, the wall thickness 312 of the outer portion 214 measured between inner surface 302 and the outer surface 304 may be between 0.1 mm and 3 mm. In one particular embodiment, the wall thickness 312 may be about 1 mm.

Figure 4:
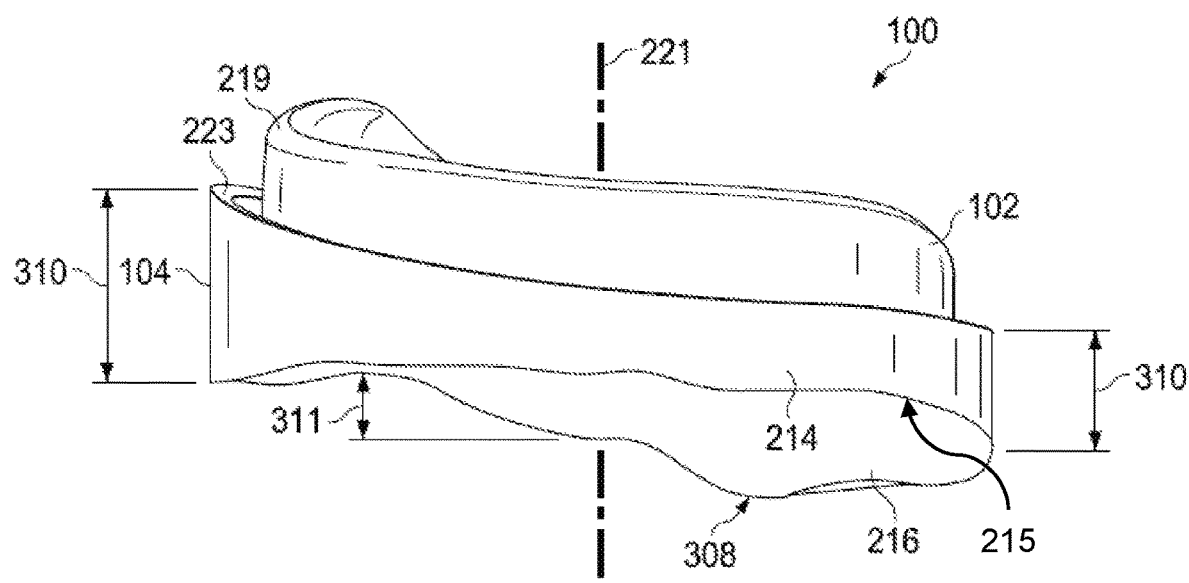
FIG. 4 is a diagrammatic perspective side view of a prosthetic meniscus device, according to an exemplary implementation.

FIG. 4 is a perspective side view of the prosthetic meniscus device 100 with a free floating meniscus component 102 disposed inside rigid base component 104, according to one embodiment. As illustrated in FIG. 4, the lower surface 308 of the bottom portion 216 in the rigid base component 104 is molded to match the shape of a bone or tissue interface, such as the shape of the native tibial plateau. As also illustrated in FIG. 4, the height 310 of the outer portion 214 varies because a lower end 215 forming a peripheral bottom edge of the outer portion 214 conforms to the nonplanar variations in the slope of lower surface 308, while the upper end 223 forming the upper edge of the outer portion 214 remains at approximately the same height with respect to upper edge 219 the free floating meniscus component 102.

In some implementations, the variation of the surface profile of the bottom surface may be measured as a surface variation or height 311 between 0.1 mm and 10 mm. This height may be measured as an axial distance along an axis 221 defined by the surface forming the outer portion 214 of the rigid base component 104. The height variations may be due to the shape of the bottom portion 216 that coincides with the lower surface 204 of the free floating meniscus component 102 and/or with the adjacent tissue structure, such as the native tibial plateau of the host knee.

Figure 5:
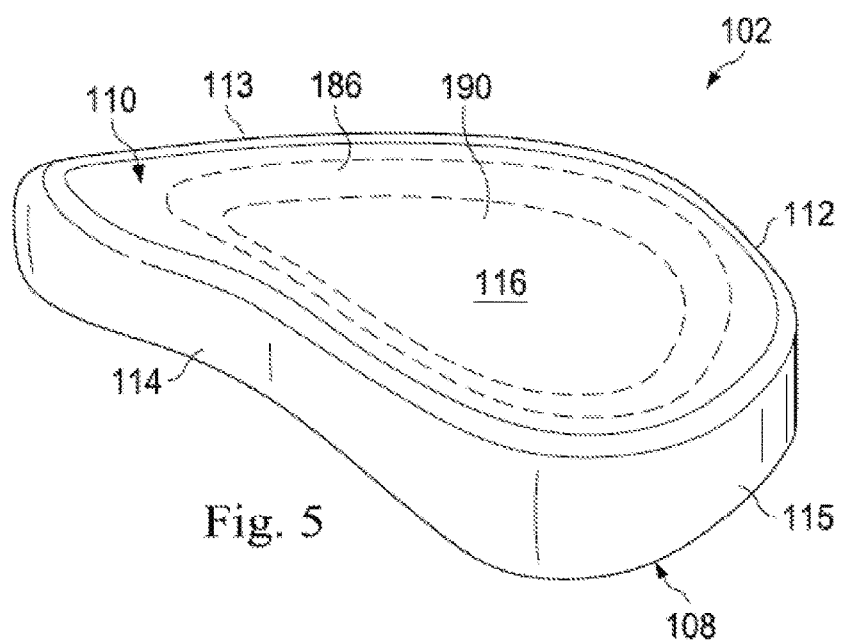
FIG. 5 is a diagrammatic perspective front view of a free floating meniscus component of a prosthetic meniscus device, according to an exemplary implementation.
Figure 6:
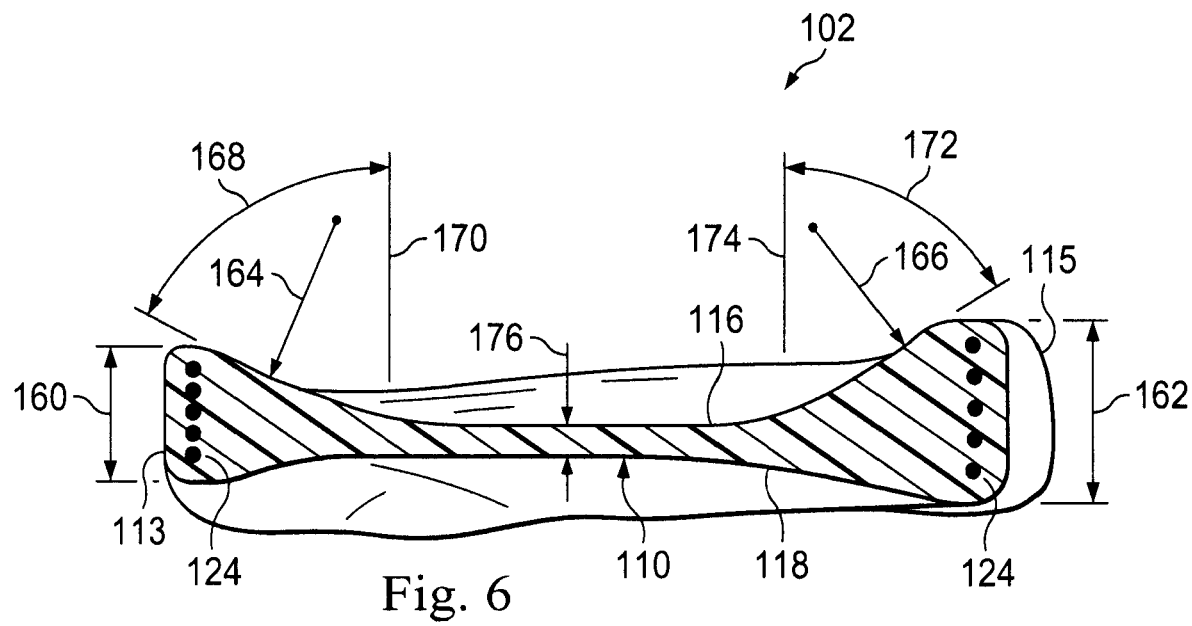
FIG. 6 is a diagrammatic cross sectional view of the free floating meniscus component of FIG. 5, according to an exemplary implementation.

FIGS. 5 and 6 show a free floating meniscus component 102 of the prosthetic meniscus device 100. Some features may be similar to a prior design set forth in U.S. Pat. No. 8,361,147, which is hereby incorporated by reference in its entirety. The body of free floating meniscus component 102 comprises an outer body portion 108 (referred to as the outer portion 206 in FIG. 2) and a central body portion 110. Generally, the outer body portion 108 has an increased thickness and height relative to the central body portion 110. In some instances the outer body portion 108 has a thickness between 5 mm and 15 mm. In some instances, the central body portion 110 has a thickness between 0.5 mm and 5 mm. In one particular embodiment, the outer body portion 108 has a maximum thickness of approximately 10 mm and the central body portion 110 has a maximum thickness of approximately 2 mm. The height or thickness of the outer body portion 108 varies around the perimeter of the prosthetic device in some instances. In that regard, the variations in the height or thickness of the outer body portion 108 are selected to match the anatomical features of the patient in some embodiments. Similarly, the height or thickness of the central body portion 110 varies across the prosthetic device in some embodiments. Again, the variations in the height or thickness of the central body portion 110 are selected to match the anatomical features of the patient in some embodiments. In some embodiments, the free floating meniscus component 102 is inserted in an insertion configuration and then loaded, stretched, moved, and/or otherwise transferred to an implantation configuration. In some implementations, the insertion configuration has a smaller profile or shape than the implantation configuration. In other implementations, the insertion configuration is simply different than the implantation configuration in order to accommodate insertion between the bones of the joint. In some embodiments the transformation between the insertion configuration and the implantation configuration is facilitated through the application of a loading force of the free floating meniscus component 102. In such embodiments, the variations in height or thickness of the outer and central body portions 108, 110 are selected to accommodate the deformation or transformation between the insertion configuration and the implantation configuration.

To this end, the outer body portion 108 of the free floating meniscus component 102 includes a first portion 112 and a second portion or bridge 114. In some embodiments, the first portion 112 substantially matches the shape of a natural meniscus. In some embodiments, the outer body portion 108 has a circular or semi-ellipsoidal shape. Accordingly, the first portion 112 extends around a majority of the outer body portion 108. The bridge 114 connects the two ends of the first portion 112. Thus, where the prosthetic device is configured for use as a medial meniscus device, the bridge 114 extends along the lateral side of the device. Where the free floating meniscus component 102 is configured for use as a lateral meniscus device, the bridge 114 extends along the medial side of the device. Accordingly, the outer body portion 108—comprised of the first portion 112 and the bridge 114 and having an increased thickness relative to the central body portion 110—completely surrounds the central body portion 110 and serves to limit movement of the prosthetic device after implantation.

The height or thickness of the bridge 114 is based on the size of the femur notch and the distance to the cruciate ligaments in some embodiments. In some embodiments, the bridge 114 has a maximum height or thickness that is between ¼ and ¾ the maximum height or thickness of the first portion 112 of the outer body portion 108. In some embodiments, the size and shape of the bridge 114 is selected to achieve an optimal pressure distribution on the native tibial plateau in order to mimic the pressure distribution of a healthy natural meniscus. The bridge 114 and, more generally, the outer body portion 108 are geometrically characterized by anterior, posterior, lateral-anterior, mid-lateral and lateral-posterior angles and heights as well as sagittal and coronal radii of curvature. Further, the outer body portion 108 and the central body portion 110 are shaped and sized such that the free floating meniscus component 102 is self-centering within rigid base component 104. That is, the shape and size of the prosthetic meniscus device itself encourages the prosthetic device to position or align itself with a desired orientation within the knee joint based on the position of the femoral surface. Accordingly, as the free floating meniscus component 102 moves through a range of positions within the knee joint, it naturally returns to the desired orientation due to the shape and size of the outer and central body portion 108, 110. In some embodiments, the outer body portion and, more specifically, the bridge 114 alone or together with rigid base component 104 acts as a physical barrier limiting the movement of the prosthetic device caused by joint reaction forces. The shape of the related femoral or tibial bearing component interacting with the self-centering or self-aligning mechanism combined with the free floating meniscus component's 102 ability to move within the knee joint results in improved location of the prosthetic meniscus device 100 during typical gait cycles (e.g., flexion-extension angles of 0° to 20° or "heel-strike" to "toe-off"). The result is that the free floating meniscus component 102 exhibits a load pressure distribution similar to that of a natural meniscus.

The central body portion 110 defines an upper surface 116 and a lower surface 118 (referred to as upper surface 202 and lower surface 204 in FIG. 2.). The upper surface 116 may interface with the tissue structure of the joint and may form a part of a bearing surface. In particular, the upper surface 116 is configured to movingly engage with a medial femoral condyle of the femur. In that regard, free floating meniscus component 102 can translate and rotate with respect to the femur and/or tibia within a range. In some instances, translation is possible in both the anterior-posterior and medial-lateral directions. In some embodiments, the upper surface 116 includes both a vertical and horizontal surface. To that end, in some embodiments the upper surface 116 comprises a concave surface that defines the vertical and horizontal surfaces. The thickness of the central body portion 110 between the upper surface 116 and the lower surface 118 supports stress distribution capability of the component, while the increased height of the upper surface 116 as it extends outwardly towards the outer body portion 108 defines the horizontal surface of the component. Similarly, in some embodiments the lower surface 118 includes both vertical and horizontal components. In particular, in some embodiments the lower surface 118 comprises a convex surface or a concave surface that is molded to the shape of the inside portion of rigid base component 104.

The thickness of the central body portion 110 between the upper surface 116 and the lower surface 118 determines the load distribution capacity of the component, while the tapered height of the lower surface 116 as it extends outwardly towards the outer body portion 108 defines the horizontal component. In some embodiments, the upper surface 116 and/or the lower surface 118 are shaped such that the component is biased towards a neutral position in the knee. For example, the arcuate profiles of the upper surface 116 and/or the lower surface 118 are shaped such that the interaction between the surfaces and the femoral surface encourages the implant to a particular orientation relative to the surfaces.

Referring to FIG. 6, shown therein is a diagrammatic cross-sectional view of free floating meniscus component 102 taken along an anterior to posterior section line between anterior end 113 and posterior end 115. The central body portion 110 is reinforced by pre-tensioned fibers 124 wound around the core to inhibit outward deformation while allowing inward flexibility. As shown, the anterior end 113 of the outer body portion 108 has an anterior height or thickness 160. In that regard, the anterior height or thickness 160 of the anterior end 113 is between about 4 mm and immediately adjacent bridge 114 could be as great as about 15 mm and, in some instances, is between about 5.7 mm and about 9.3 mm. In the illustrated embodiment, the anterior height or thickness 160 of the anterior end 113 is approximately 7.8 mm. In a smaller embodiment, the anterior height or thickness 160 is approximately 5.7 mm. In a larger embodiment, the anterior height or thickness 160 is approximately 9.3 mm. The posterior height or thickness 162 of the posterior end is between about 4 mm and immediately adjacent the bridge 114 could be as great as about 20 mm and, in some instances, is between about 7.7 mm and about 12.7 mm. In the embodiment, the posterior height or thickness 162 of the posterior end 115 is approximately 9.0 mm. In a smaller embodiment, the posterior height or thickness 162 is approximately 7.7 mm. In a larger embodiment, the posterior height or thickness 162 is approximately 12.7 mm.

The anterior portion of the upper surface of the anterior end 113 has an anterior radius of curvature 164. In that regard, the anterior radius of curvature 164 is between about 10 mm and about 100 mm and, in some instances, is between about 23.0 mm and about 33.1 mm. In the embodiment, the radius of curvature 164 is approximately 72 mm. In another embodiment, the radius of curvature 164 is approximately 28 mm. In a smaller embodiment, the radius of curvature 164 is approximately 23 mm. In a larger embodiment, the radius of curvature 164 is approximately 33.1 mm. The posterior portion of the upper surface of the posterior end 115 has a posterior radius of curvature 166. In that regard, the posterior radius of curvature 166 is between about 5 mm and about 70 mm and, in some instances, is between about 15.2 mm and about 24.2 mm. In the illustrated embodiment, the radius of curvature 166 is approximately 30 mm. In a smaller embodiment, the radius of curvature 166 is approximately 15.2 mm. In a larger embodiment, the radius of curvature 166 is approximately 24.2 mm.

Further, the anterior portion 113 of the upper surface generally extends at an anterior angle 168 with respect to an axis 170 extending substantially perpendicular to a plane generally defined by the free floating meniscus component 102, as shown. The anterior angle 168 is between about 45 degrees and about 75 degrees and, in some instances, is between about 62 degrees and about 68 degrees. In the illustrated embodiment, the angle 168 is approximately 65 degrees. In a smaller embodiment, the angle 168 is approximately 62 degrees. In a larger embodiment, the angle is approximately 68 degrees. The posterior end 115 of the upper surface generally extends at an posterior angle 172 with respect to an axis 174 extending substantially perpendicular to a plane generally defined by the prosthetic meniscus device 100, as shown. The posterior angle 172 is between about 35 degrees and about 70 degrees and, in some instances, is between about 55 degrees and about 61 degrees. In the embodiment, the angle 172 is approximately 58 degrees. In a smaller embodiment, the angle 172 is approximately 50 degrees. In a larger embodiment, the angle 172 is approximately 65 degrees.

The central body portion 110 has a height or thickness 176 between the articulating upper surface 116 and the articulating lower surface 118. In some embodiments, the height or thickness 176 is the minimal thickness of the central body portion 110 and, in more specific embodiments, the minimal thickness of the entire free floating meniscus component 102. To that end, the height or thickness 176 is between about 1 mm and about 3 mm and, in some instances, is between about 1.2 mm and about 2.1 mm. In the embodiment, the height or thickness 176 is approximately 1.5 mm. In a smaller embodiment, the height or thickness 176 is approximately 1.2 mm. In a larger embodiment, the height or thickness 176 is approximately 2.1 mm.

Figure 7:
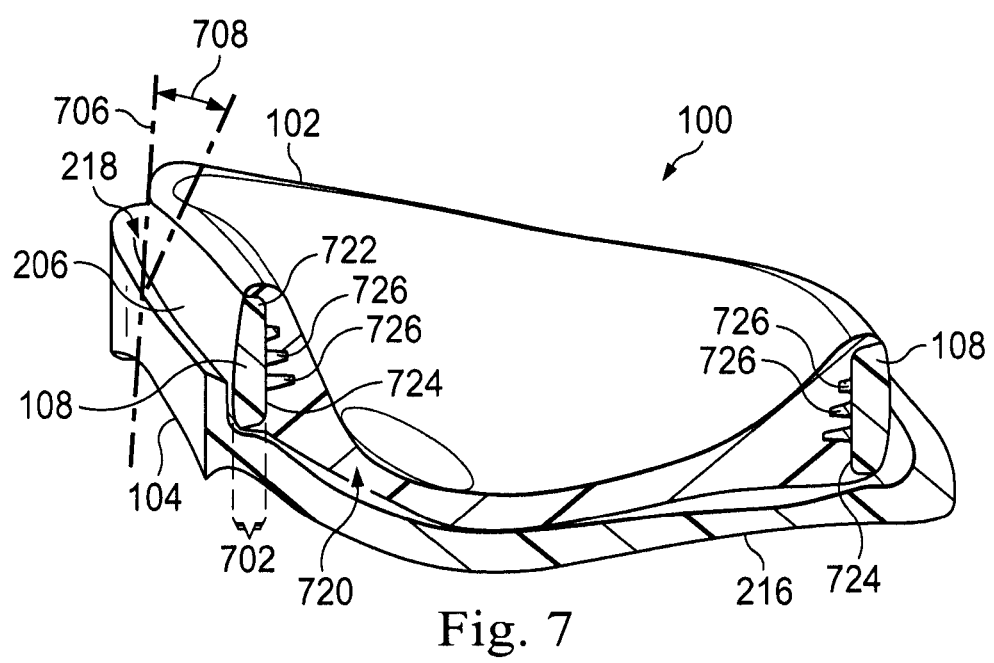
FIG. 7 is a diagrammatic cross sectional view of a free floating meniscus component in a rigid base component, according to an exemplary implementation.

FIG. 7 is a cross-sectional view of the prosthetic meniscus device 100 with the free floating meniscus component 102 disposed inside the containment cavity 217 of the rigid base component 104. As illustrated in FIG. 7, the bottom portion 216 of rigid base component 104 is adjacent to the outer body portion 108 of the free floating meniscus component 102. As also illustrated in FIG. 7, the bottom portion 216 of the rigid base component 104 may have a generally concave shape. In some implementations, the bottom portion 216 is shaped to form fit or receive the surface of the outer body portion 108. As also illustrated in FIG. 7, the bottom portion 216 may have an edge portion 702 that extends along the outer edge of the bottom portion 216.

As discussed above, the free floating meniscus component 102 and the rigid base component 104 may be sized so that the outer portion 206 of the free floating meniscus component 102 and the outer portion 214 of the rigid base component 104 may be separated by the gap or space 218. This gap or space 218 may permit the free floating meniscus component 102 to rotate or translate within the rigid base component 104. In one embodiment, the outer portion 206 and the outer portion 214 may have outer surfaces generally parallel to each other along axis 706 extending substantially perpendicular to a plane generally defined through the prosthetic meniscus device 100, as shown. In another embodiment, outer portion 206 generally extends at angle 708 with respect to axis 706 away from the outer portion 214 and toward the center of the free floating meniscus component 102. Depending upon the implementation, the angle 708 is between 0 degrees and 45 degrees. In some implementations, the angle 708 is between 5 degrees and 20 degrees.

FIG. 7 shows an exemplary implementation of the free floating meniscus component 102. In this implementation, the free floating meniscus component 102 comprises a bearing portion 720 cooperatively joined with a peripheral support portion 722. In this implementation, the peripheral support portion 722 forms outer body portion 108 described herein. Here, the bearing portion 720 comprises the upper surface 202 and the lower surface 204, and is configured to interface with tissue at the joint and provide bearing support for weight at the joint.

In this implementation, the bearing portion 720 comprises outer edges 724 that abut against the peripheral support portion 722. These outer edges 724 comprise tension apertures 726. In this implementation, the tension apertures 726 extend fully around the periphery at the outer edge 724 of the bearing portion 720. In some implementations, the tension apertures 726 may receive fibers (not shown in FIG. 7), similar to or the same as the pre-tensioned fibers 124 in FIG. 6. Such fibers may wind around the bearing portion 720 in the tension apertures 726 to inhibit outward deformation while allowing inward flexibility. In other implementations, instead of fibers, alternative reinforcement material may be introduced or embedded in the tension apertures 726. Some implementations are devoid of tension apertures 726.

The peripheral support portion 722 may be structurally embedded in a portion of the bearing portion 720 so as to be partially enveloped in the bearing portion 720 as shown in FIG. 7. In some implementations, the peripheral support portion 722 may be formed of a more rigid material than the bearing portion 720, and may provide rigidity and strength to the free floating meniscus component 102. In the implementation shown, edges of the bearing portion 720 and develop an interface with the upper and lower surfaces of the peripheral support portion 722. However, other arrangements may be used to securely maintain the peripheral support portion 722 in place about the bearing portion 720. In some implementations, the bearing portion 720 and the peripheral support portion 722 are formed of the same material. In one exemplary implementation, the peripheral support portion 722 may have one or more extending ridges, hooks, or notches that may extend into one or more of the tension apertures 726. In some implementations, the ridges, hooks, or notches may extend into other grooves or reception cavities formed in the outer edge of the bearing portion 720. These types of arrangements may provide mechanical interference that prevents the bearing portion 720 from displacing vertically relative to the peripheral support portion 722.

In use, under a bearing load, the bearing portion 720 of the free floating meniscus component 102 may be formed to match the profile of the more rigid bottom portion 216 of the rigid base component 104. Accordingly, although gaps are shown between the lower surface 204 of the free floating meniscus component and the upper surface 306 of the rigid base component, under load, these gaps may be minimized or reduced. Furthermore, under load, the concave cavity of the free floating meniscus component 102 may change shape slightly, such as the radius of curvature may be increased as a result of the applied loading. Additionally, the outer edges 724 of the bearing portion 720 may apply loading on the peripheral support portion 722, causing some deformation or expansion of the peripheral support portion 722. As discussed above, fibers or other materials may be used to limit, restrain, or control, the amount of deformation permitted under a load.

Figure 8A:
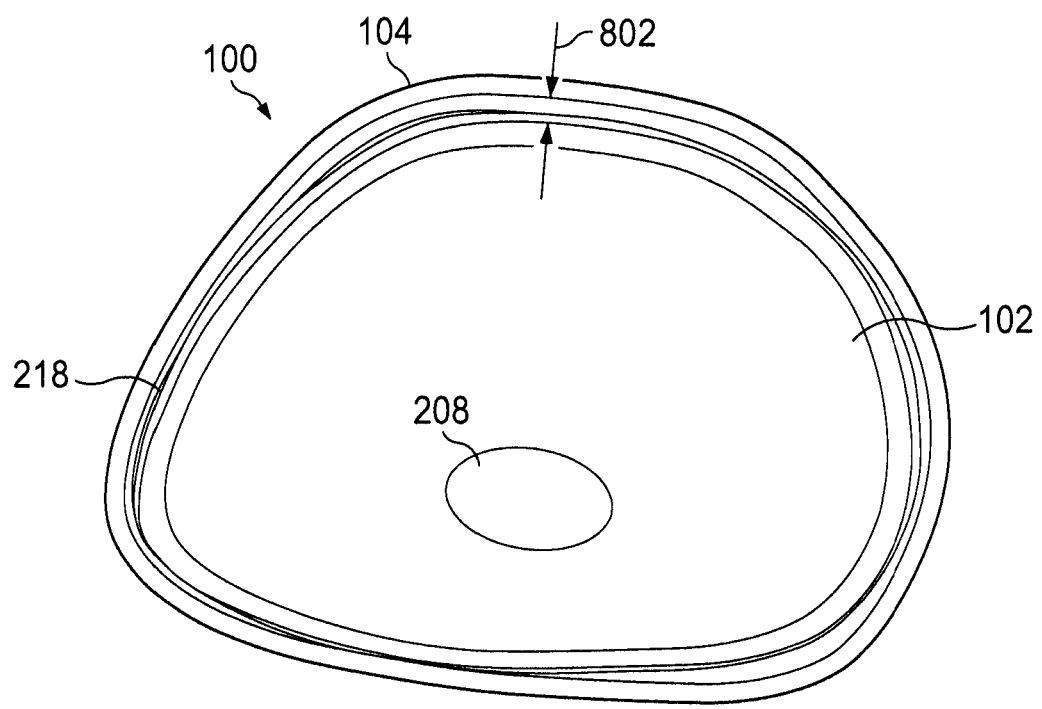
FIGS. 8A and 8B are diagrammatic perspective top and side views of the prosthetic meniscus device, according to an exemplary implementation.
Figure 8B:
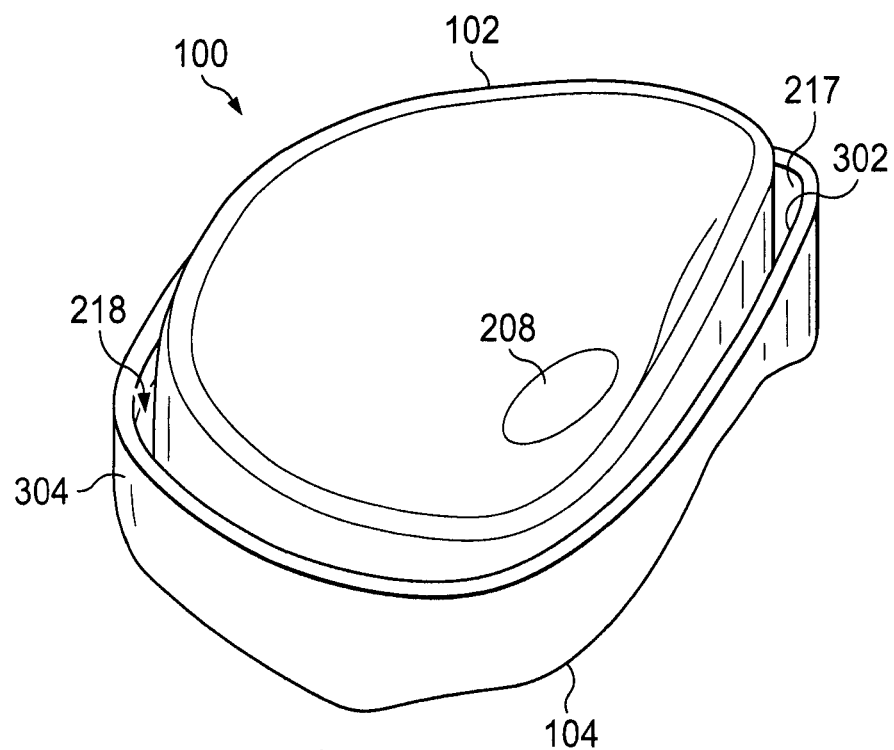

FIGS. 8A and 8B are top and side perspective views of the prosthetic meniscus device 100 with the free floating meniscus component 102 disposed inside the rigid base component 104, according to an exemplary implementation. As illustrated in FIGS. 8A and 8B, the free floating meniscus component 102 may have a circular or semi-elliptical shape, and is disposed inside rigid base component 104 that may also have a circular or semi-elliptical shape that generally conforms to the shape of rigid base component 104. As also illustrated in FIGS. 8A and 8B, gap or space 218 is maintained between components 102 and 104, but may vary in width 802 in order to allow the free floating meniscus component 102 to float inside rigid base component 104. In some embodiments, the width 802 of may fall within the range of between 0.05 mm and 3 mm. In some implementations, width 802 may change as the free floating meniscus component 102 floats inside the rigid base component 104 as the knee is in motion.

As discussed above, the prosthetic meniscus device 100 is a minimally invasive implant that floats inside the medial compartment of the knee joint and prevents further damage to the meniscus and/or other tissues like cartilage articulating surfaces. The prosthetic meniscus device 100 may also protect a structural carrier, such as morsalized bone or a cartilage matrix, which may include a biologic, that may be introduced in the medial femoral condyle to promote tissue regeneration and regrowth of the damaged cartilage. In some implementations, the prosthetic meniscus device 100 may be implanted into the native tibial plateau of the host knee such that the free floating meniscus component 102 engages the femoral surface and redistributes weight load transmitted across the knee joint, while the rigid base component 104 engages the natural tibial plateau and prevents the free floating meniscus component 102 from being unintentionally expelled from the knee joint. As discussed above, the free floating meniscus component 102 may be modified to have limited contact with one or more portions of the femoral surface as dictated by the treatment. For example, when the damaged area of the medial femoral condyle has been treated with a biologic or stem cell paste to allow cartilage to regenerate and regrow, the free floating meniscus component 102 may include one or more bone-relief recess areas, such as bone-relief recess area 208 that limits contact between the prosthetic meniscus device 100 and the treated areas of the medial femoral condyle. Depending upon the implementation, the bone relief recess areas may be custom formed to match individual patients or conditions.

In a further embodiment, the free floating meniscus component 102 with the bone-relief recess area 208 may be swapped out or exchanged for another free floating meniscus component 102 with a different bone-relief recess area 208 or for the free floating meniscus component 102 with a smooth upper surface 202. For example, once the medial femoral condyle has healed and the cartilage had regrown, the free floating meniscus component 102 with the bone-relief recess area 208 may be exchanged in a revision surgery for the free floating meniscus component 102 with the smooth upper surface 202.

Figure 9:
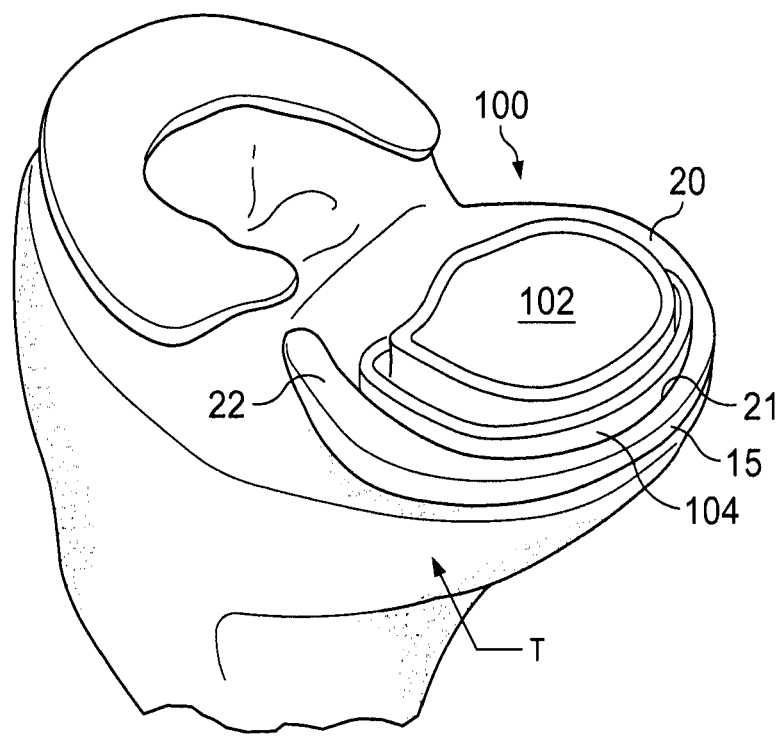
FIG. 9 is a diagrammatic perspective view of a free floating meniscus component disposed on a tibia according to an exemplary implementation.

FIG. 9 shows an example illustration of the prosthetic meniscus device 100 disposed upon the tibia T of a knee joint with an injured meniscus 10. The meniscus includes an outer rim 15 that is anchored to the bone along the posterior rim 20 and the anterior rim 22. The meniscus may form a meniscus pocket defined by a sidewall 21 of the meniscus, and in which the prosthetic meniscus device 100 may be disposed. The prosthetic meniscus device 100 engages not only the tibia T, but also the Femur (not shown in FIG. 9.)

In some implementations, the prosthetic meniscus device 100 may be implanted in a two-step process. In the first step, only a temporary free floating meniscus component 102 may be implanted into the knee joint. The implanted free floating meniscus component 102 may comprise a smooth upper surface 202 or have one or more bone-relief recess areas, such as bone-relief recess area 208 formed, such as by etching, on the upper surface 202, depending on the treatment. For example, a patient may be required to gradually apply pressure on the cartilage in the knee following a minimally invasive surgery in order for the cartilage to regrow and have necessary density, as described above. The free floating meniscus component 102 having a smooth upper surface 202 with the bone-relief recess area 208 opposite the areas in the medial femoral condyle where the cartilage is being regrown, allows the patient to apply pressure across the entire knee joint, including the areas where the cartilage is being regrown, yet limits the physical contact with these areas and the free floating meniscus component 102.

In some implementations, the second step of the two-step surgical process may be performed days, weeks, or months after the first step of the surgical process. This may allow some healing to occur prior to the second step. For example, the second step of the two-step surgical process may be performed after cartilage has begun growing on the medial femoral condyle or other bone structure. In the second step, the free floating meniscus component 102 may be replaced with a full prosthetic meniscus device 100, including the free floating meniscus component 102 and the rigid base component 104. The free floating meniscus component 102 can be the same or different free floating meniscus component 102 as in the first step. In some implementations, the free floating meniscus component 102 may have a smooth upper surface 202. As indicated herein, the second step generally occurs after the cartridge has healed or has been regrown and the prosthetic meniscus device 100 is implanted into the knee joint for the long term use by the patient.

Figure 10A:
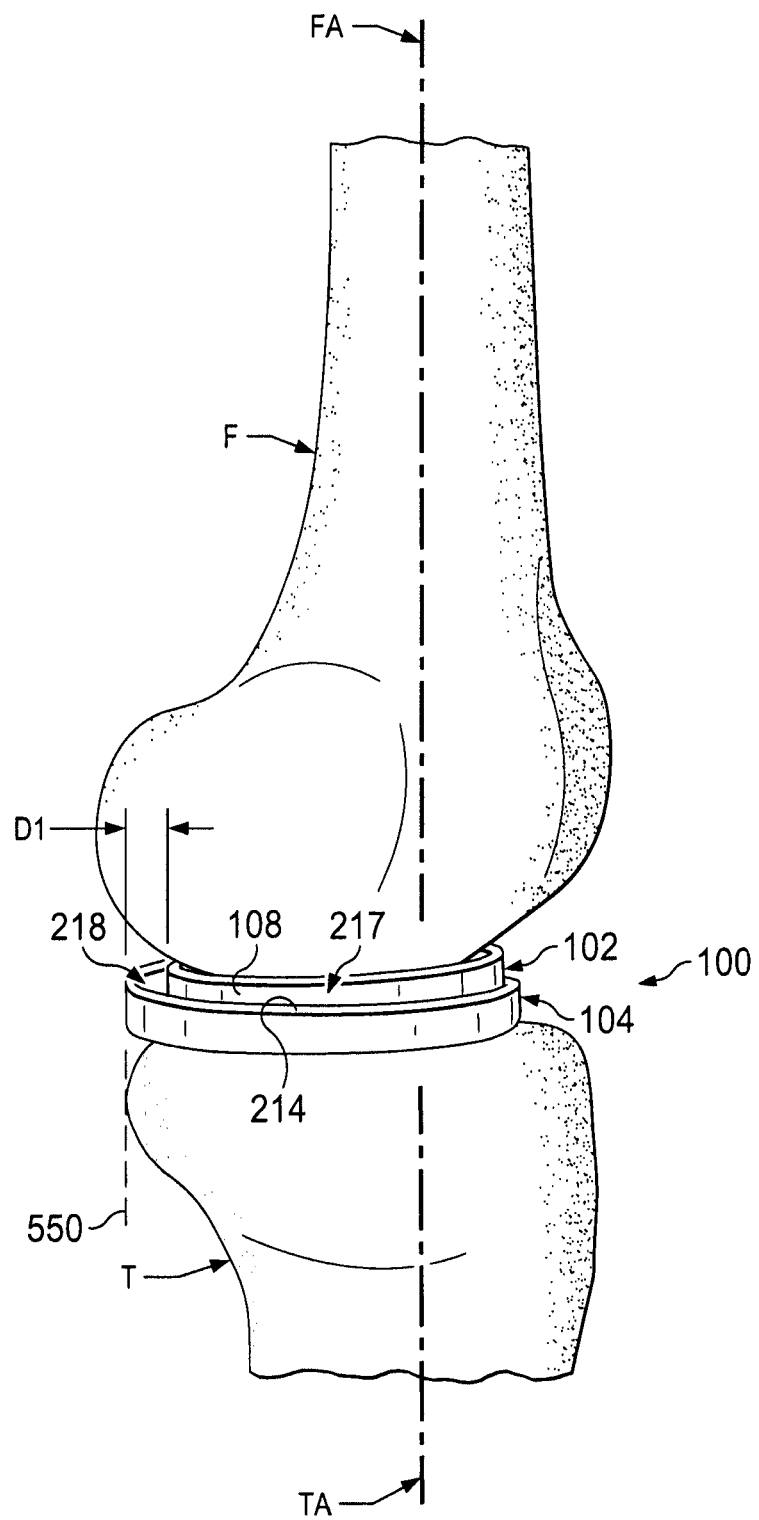
FIGS. 10A, 10B, 10C, and 10D are diagrammatic illustrations of an implanted free floating meniscus component with the knee articulated through a series of angles.

FIGS. 10A, 10B, 10C, and 10D show a series of angular positions of the femur in relation to the tibia and the correspondent movement of the prosthetic meniscus device 100 in the knee joint. In FIG. 10A, femoral axis FA is substantially aligned with the tibial axis TA. The prosthetic meniscus device 100 is disposed between the tibia T and the femur F. In this initial position, with the axes FA and TA substantially aligned, the outer surface of the outer portion 214 of the rigid base component 104 may be generally aligned with a posterior wall of the joint, referenced by the reference line 550. In this position, the posterior gap or space 218 between the outer portion 214 of the rigid base component and the outer body portion 108 of the free floating meniscus component 102 is indicated by the reference number D1.

Figure 10B:
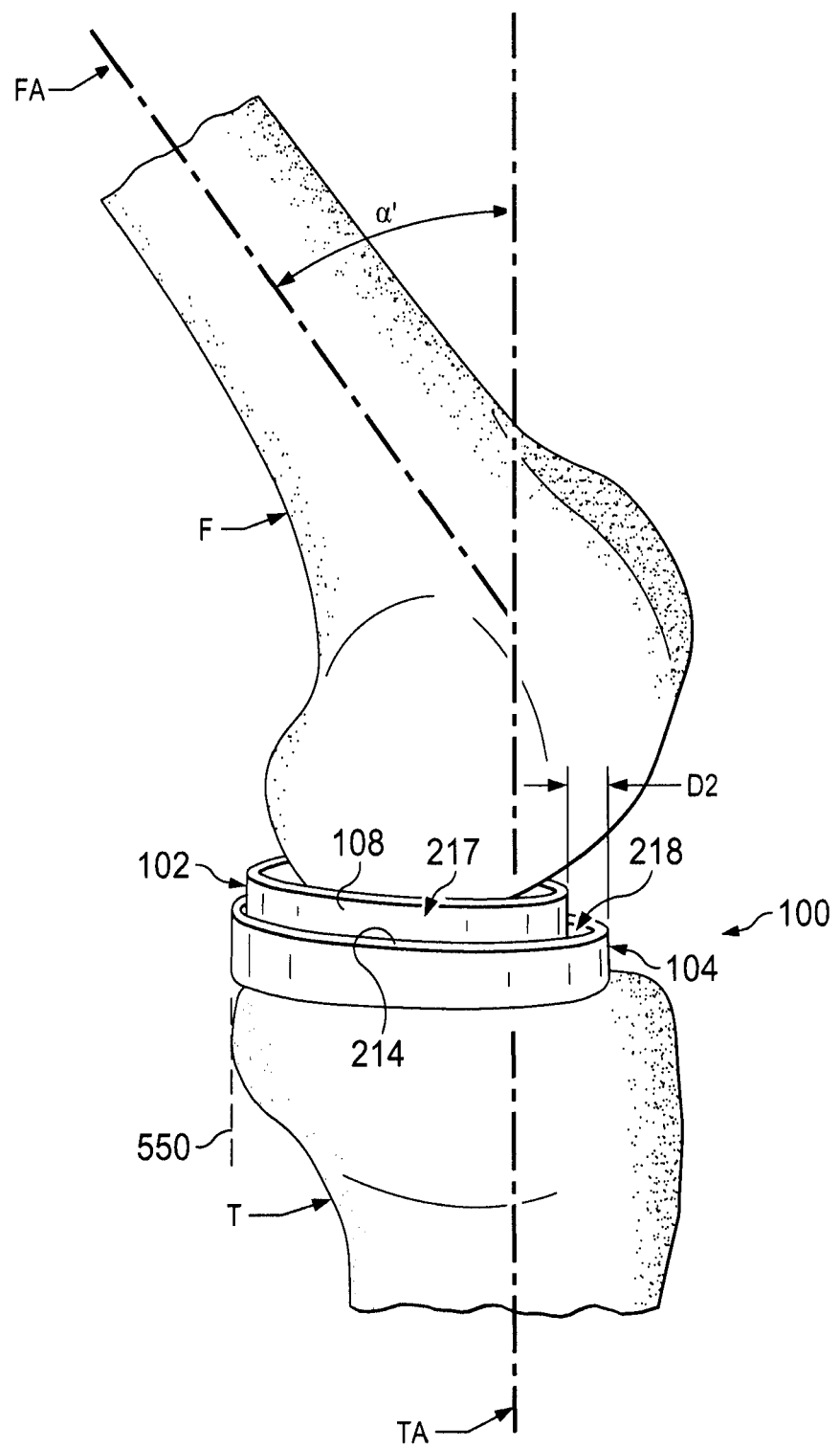

FIG. 10B illustrates the movement of the prosthetic meniscus device 100 as the femur F is moved to the position of the angle α' between axis FA and axis TA. A comparison of FIGS. 10B and 10A shows that the rigid base component 104 is maintained substantially in place, while the free floating meniscus component 102 has displaced within the containment cavity 217 of the rigid base component 104. In this instance, the free floating meniscus component 102 may have moved in the posterior direction as far as it is able. That is, it may have displaced to the point that the outer body portion 108 of the free floating meniscus component has engaged the outer portion 214 of the rigid base component 104. Because of this lateral translation, the gap or space 218 is shown now on the interior side of the joint. In this instance, the gap or space 218 is indicated by the reference number D2, which will equal D1 in FIG. 10A so long as rotation is limited. Accordingly, D2 in FIG. 10B is equal to or substantially equal to D1 in FIG. 10A.

Figure 10C:
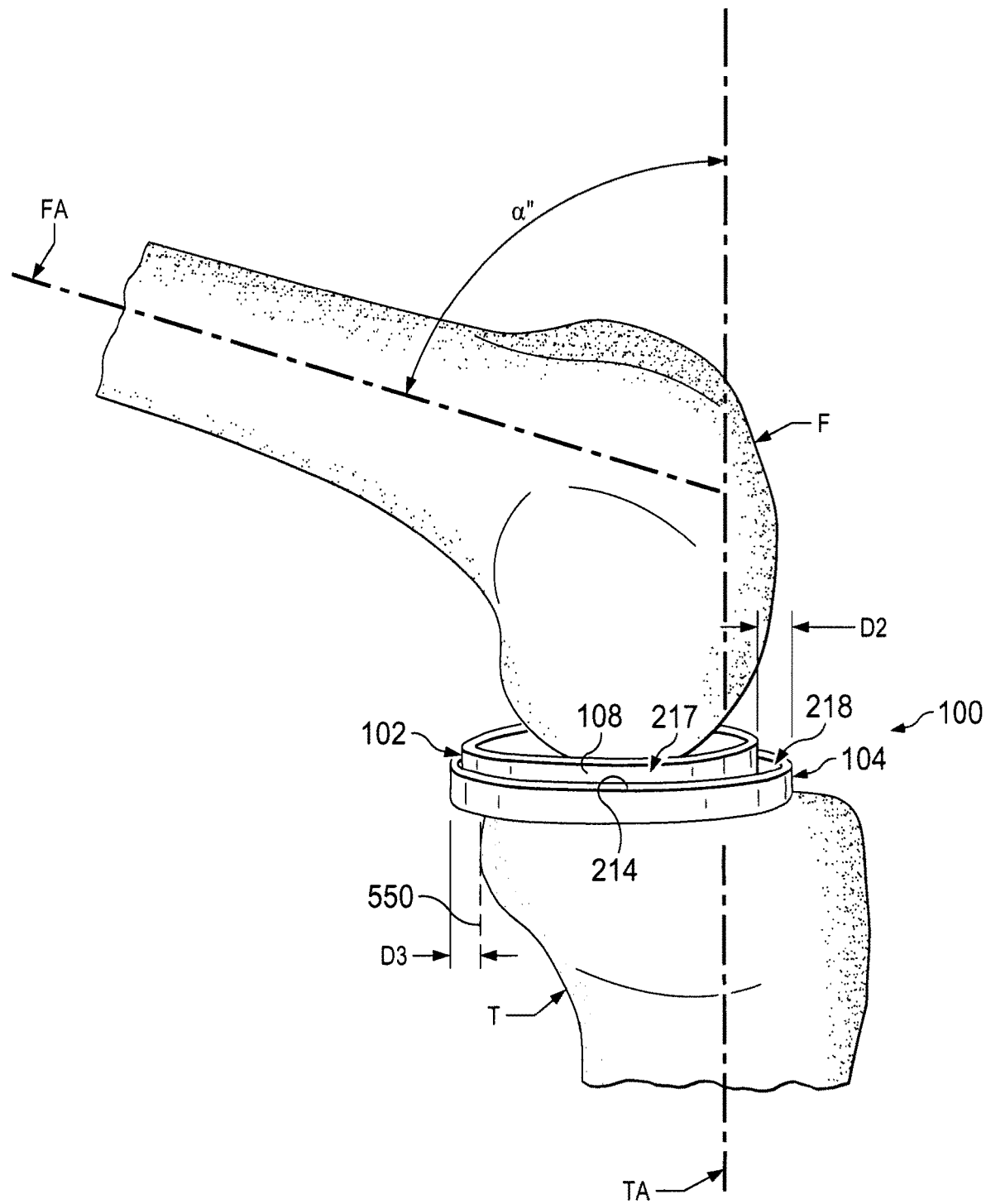

FIG. 10C illustrates the continued rotation of the femur with respect to the tibia results in angle α" which is greater than angle α'. A comparison of FIGS. 10B and 10C shows that the rigid base component 104, which is also free floating, begins displacing in the posterior direction a distance D3.

Figure 10D:
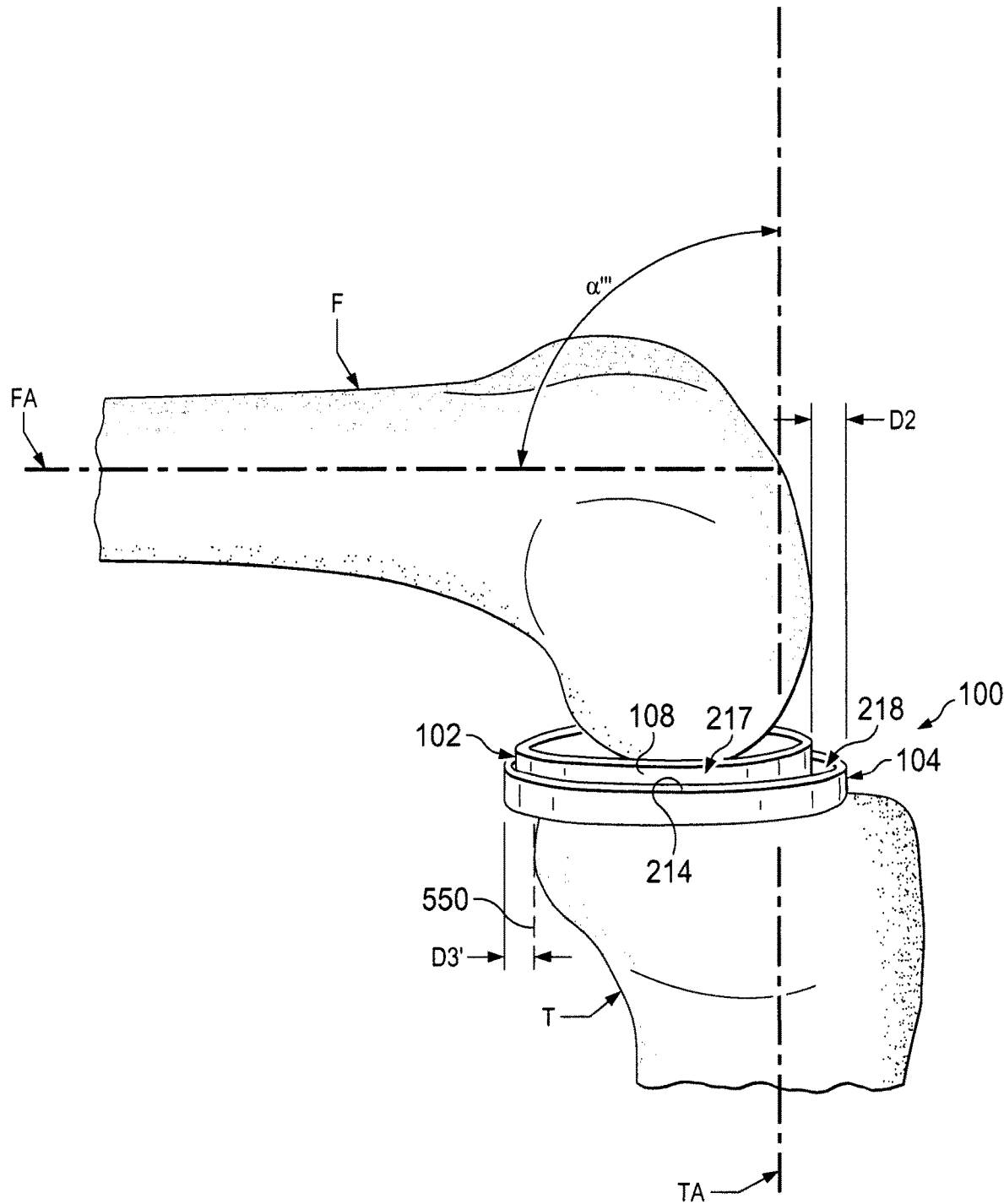

FIG. 10D illustrates that continued rotation of the femur with respect to the tibia to angle α''', which is substantially 90 degrees, results in further translation to a distance D3' which is greater than D3.

While the foregoing are not limiting, the total translation distance can range from 3-20 mm in the anterior to posterior plane, with one embodiment having D1 and D2 of 3 mm, D3 of 7 mm and D3' of 14 mm. Similarly, the rotational angle can range, without limitation, from 3 to 30 degrees of total angular rotation. An advantage of the free floating system comes because the prosthetic device may also rotate in the joint as the angle of the femur and tibia changes.

Figure 11A:
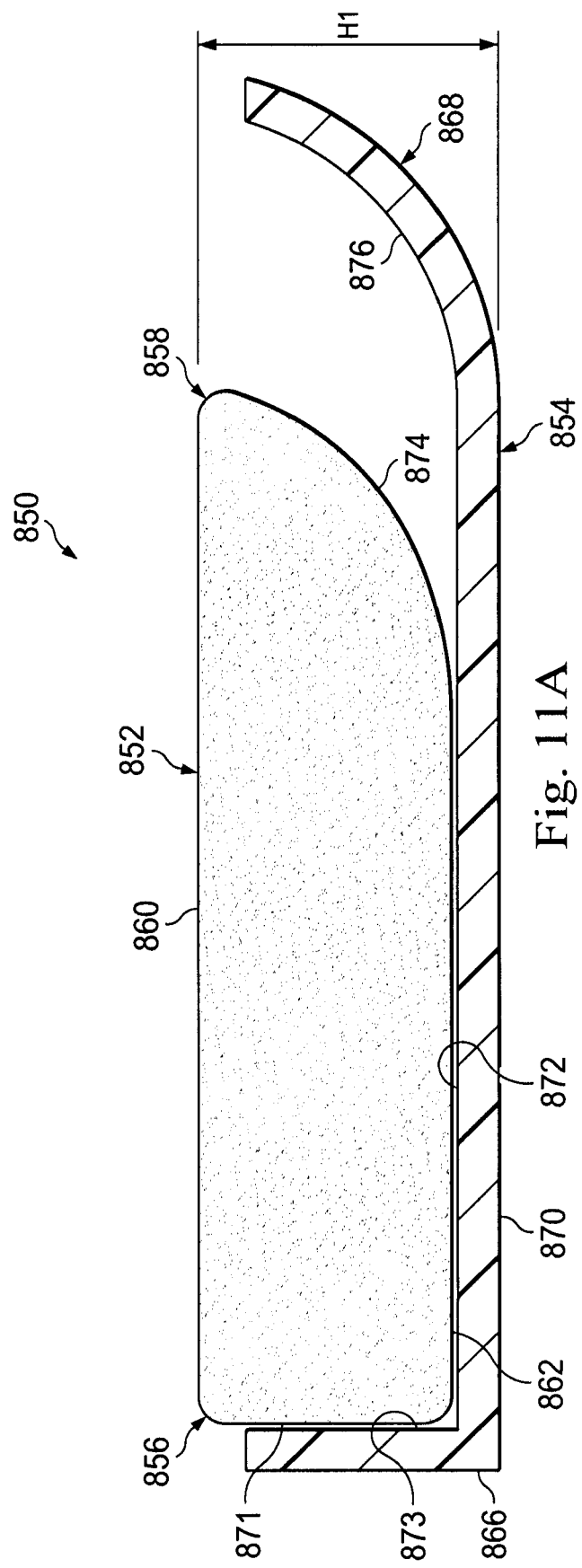
Figure 11B:
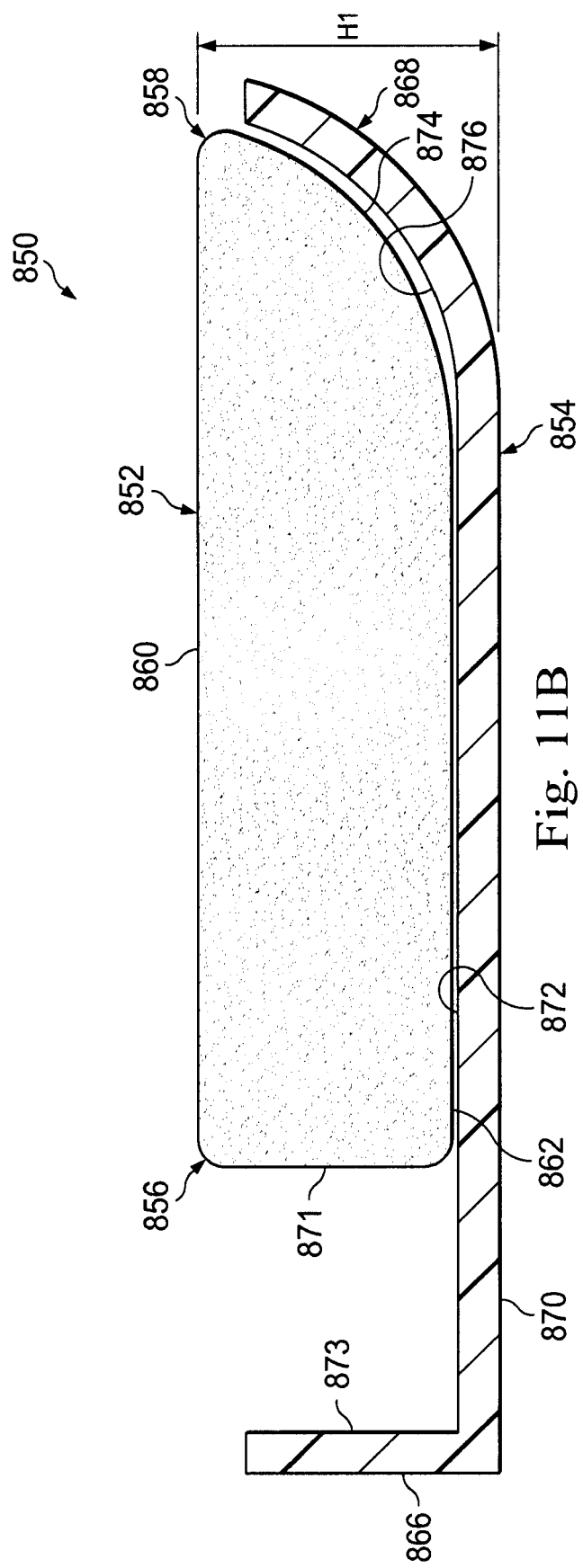

FIGS. 11A, 11B, and 11C disclose cross-sectional side views of a prosthetic meniscus device 850. Similar to the device 100 described above, the prosthetic meniscus device 850 may include a floating meniscus component 852 and a rigid base component 854. In this implementation however, the free floating meniscus component 852 and the rigid base component 854 have a particular shape that may provide biofeedback such as tactile feedback to a patient when the joint articulation begins to exceed a desired amount. In the implementation shown, the particular shape provides an abrupt backstop to prevent the free floating meniscus component 852 from translating beyond a desired position in the posterior direction. The particular shape also provides an increasing or gradual resistance to anterior displacement of the free floating meniscus component 852 relative to the rigid base component 854.

The prosthetic meniscus device 850 may be shaped generally in the same manner described herein with reference to the prosthetic meniscus device 100, but with some modifications described with reference to FIGS. 11A-11C FIG. 11A shows a cross-sectional view of the prosthetic meniscus device 850 with the free floating meniscus component 852 disposed in the cup-shaped rigid base component 854. As can be seen, the peripheral edges of the free floating meniscus component 852 and the rigid base component 854 are modified from other devices described herein. The free floating meniscus component 852 includes a posterior peripheral portion 856 and an anterior peripheral portion 858. It also includes a sliding bone or tissue interface surface 860 and a sliding interface 862. Likewise, the rigid base component 854 includes a posterior peripheral portion 866, and anterior peripheral portion 868, a tissue interface surface 870, and a sliding interface 872. As shown in FIG. 11A, the prosthetic meniscus device 850 has a height H1 when the free floating meniscus component 852 is disposed such that the sliding interface 862 and the sliding interface 872 are engaged at their lowest portions. The height H1 may be measured from the tissue interface surface 870 to the tissue interface surface 860.

The posterior peripheral portion 856 of the free floating meniscus component 852 includes a substantially vertical peripheral edge 871. Likewise the posterior peripheral portion 866 of the rigid base component 854 includes a substantially vertical peripheral edge 873. As such, when the free floating meniscus component 852 slides and abuts against the posterior peripheral portion 866, the free floating meniscus component may come to an abrupt stop. Also, when the free floating meniscus component 852 is disposed posteriorly in the rigid base component 854, the prosthetic meniscus device 850 has the height H1.

The anterior peripheral portion 858 of the free floating meniscus component 852 includes a curved or tapered edge 874. The curved edge 874 extends from an upper portion of the free floating meniscus component and tapers inwardly. The anterior peripheral portion 868 of the rigid base component 854 also includes a curved or tapered edge 876. In some implementations, such as the one shown in FIG. 11A, the curved or tapered edge is disposed on both the interior portion and the exterior portion of the rigid base component 854. That is, the interior and exterior profiles of the rigid base component 854 substantially match. In other implementations, the curved or tapered edge 876 is disposed only on the interior portion of the rigid base component 854. That is, the exterior profile of the rigid base component 854 may not match the interior profile of the rigid base component 854. The purpose of the curved or tapered edges of the anterior peripheral portions 858 and 868 will become apparent with reference to FIGS. 11B and 11C.

FIG. 11B shows the prosthetic meniscus device 850 with the free floating meniscus component 852 translated toward the anterior peripheral portion 868 of the rigid base component 854. In this exemplary embodiment, the profile of the anterior peripheral portion 858 of the free floating meniscus component 852 and the profile of the anterior peripheral portion 868 of the rigid base component 854 substantially correspond to one another. In other embodiments, the profiles of the anterior peripheral portions may not match. In some implementations, the location of the free floating meniscus component 852 at the anterior portion of the rigid base component 854 may represent a preferred distal position. Thus, in some implementations, the rigid base component 854 is sized to permit the free floating meniscus component 852 to translate from the location shown in FIG. 11A to the location shown in FIG. 11B. In some implementations, this may be determined to be a standard or typical amount of translation as the knee articulates about the joint.

FIG. 11C shows the prosthetic meniscus device 850 with the free floating meniscus component 852 translated past the position shown in FIG. 11B. Likewise, the free floating meniscus component 852 may be translated to a location beyond that found during normal acceptable knee articulation. As can be seen, as the free floating meniscus component 852 begins to translate along the sloped or angled edge 876 of the anterior peripheral portion 868 of the rigid base component, the leading anterior edge of the free floating meniscus component 852 rises, thereby changing the overall height of the prosthetic meniscus device 850. FIG. 11C shows the original height H1 and the increased height H2 which represents the overall height of the prosthetic meniscus device 850 when the free floating meniscus component 852 has moved beyond a typical or normal level of displacement on the rigid base component 854.

As can be seen, posterior motion of the free floating meniscus component 852 reaches a hard stop when the posterior peripheral portion 856 abuts against the posterior peripheral portion 866. This is because these two components each have substantially vertical surfaces causing an abrupt stop when they meet. In contrast, the anterior peripheral portion 858 and the anterior peripheral portion 868 provide a gradual stop. The sloped or angled leading surfaces cause a vertical displacement of the free floating meniscus component 852 relative to the rigid base component 854. In this implementation, the sloped or angled leading surface of the anterior peripheral portion 868 has a curvature. This curvature provides a nonlinear increase in height from H1 to H2. Some implementations use planar ramps that may provide a linear increase in height. Other implementations use a series of planar ramps with different angles.

In some implementations, this vertical displacement may be felt or noticeable by the patient as tactile biofeedback in the knee. This tactile biofeedback, along with the increasing resistance to further motion, may alert a patient to an overextension condition. Furthermore, because the prosthetic meniscus device 850 includes a gradual stop rather than an abrupt stop, the motion obtained by the prosthetic meniscus device 850 may be more consistent with the motion of a natural meniscus, where slightly elastic ligaments gradually tighten during rotation to prevent over-rotation, instead of having an abrupt, inflexible stopping point. Accordingly, the vertical displacement of the free floating meniscus component 852 may tactilely alert the patient to overextension giving the patient an opportunity to correct the knee to alleviate the tension generated by the vertical displacement. So doing may enable the patient to avoid inadvertent over displacement of the prosthetic meniscus device 850, which may help the patient avoid expulsion of the prosthetic meniscus device 850 from the patient's knee.

Although shown with having both the free floating meniscus component 852 and the rigid base component 854 having matching profiles or edges 874, 876 at the anterior peripheral portions 858, 868, other implementations have profiles or edges that do not match. In some implementations, the rigid base component 854 may have a simple planar slope as its edge 876 at its anterior peripheral portion 868. In other implementations, the anterior peripheral portion 858 of the free floating meniscus component 852 may have a substantially vertical profile at the edge 874, and the anterior peripheral portion 868 of the rigid base component 854 may have a curved or sloped edge 876. In some implementations, the vertical displacement between height H1 and height H2 may be in the range of 1 mm to 12 mm. Other ranges, both larger and smaller, are also contemplated.

Figure 12:
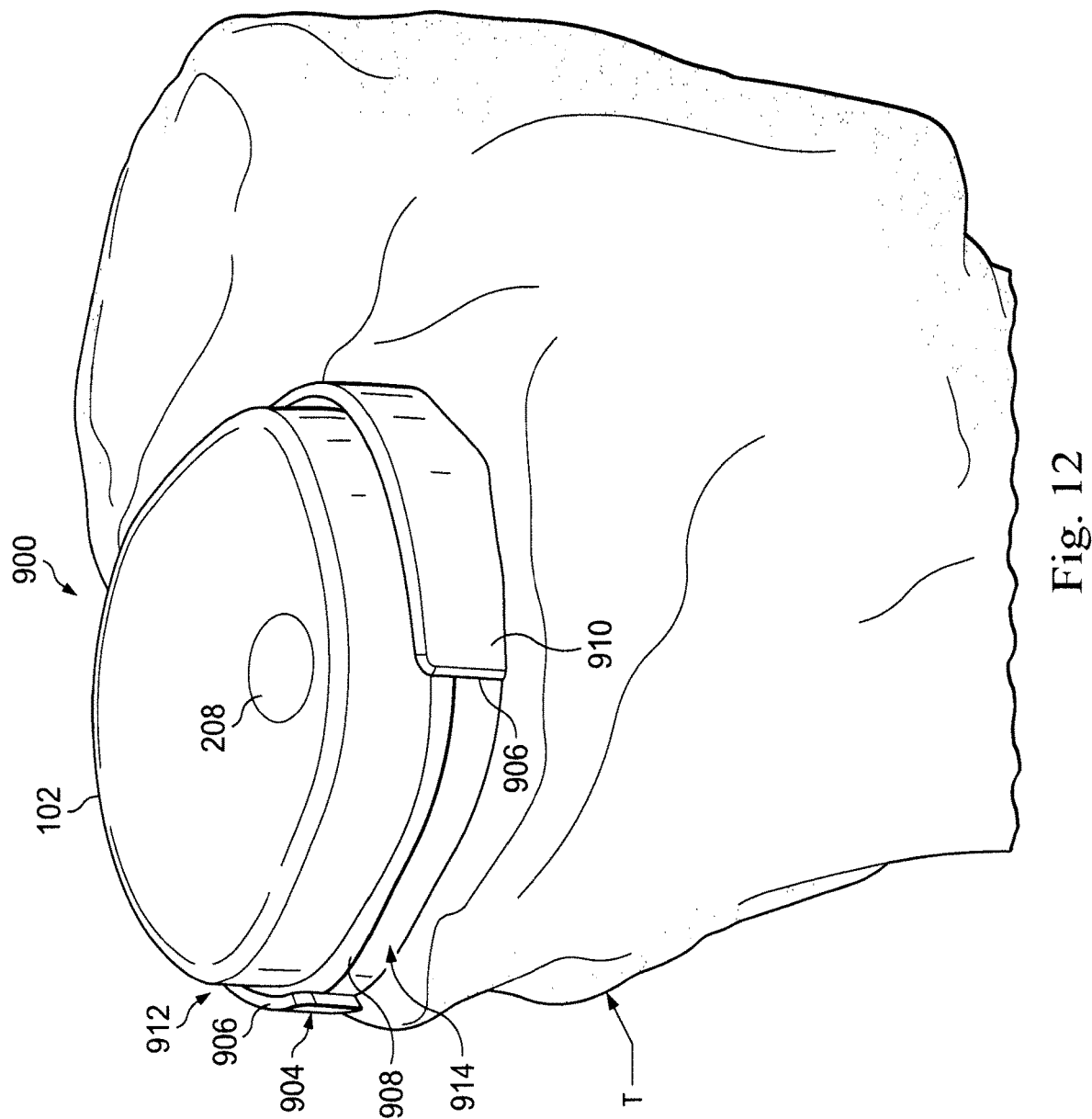
FIG. 12 is a diagrammatic perspective view of a free floating meniscus component disposed on a tibia according to an exemplary implementation.
Figure 13:
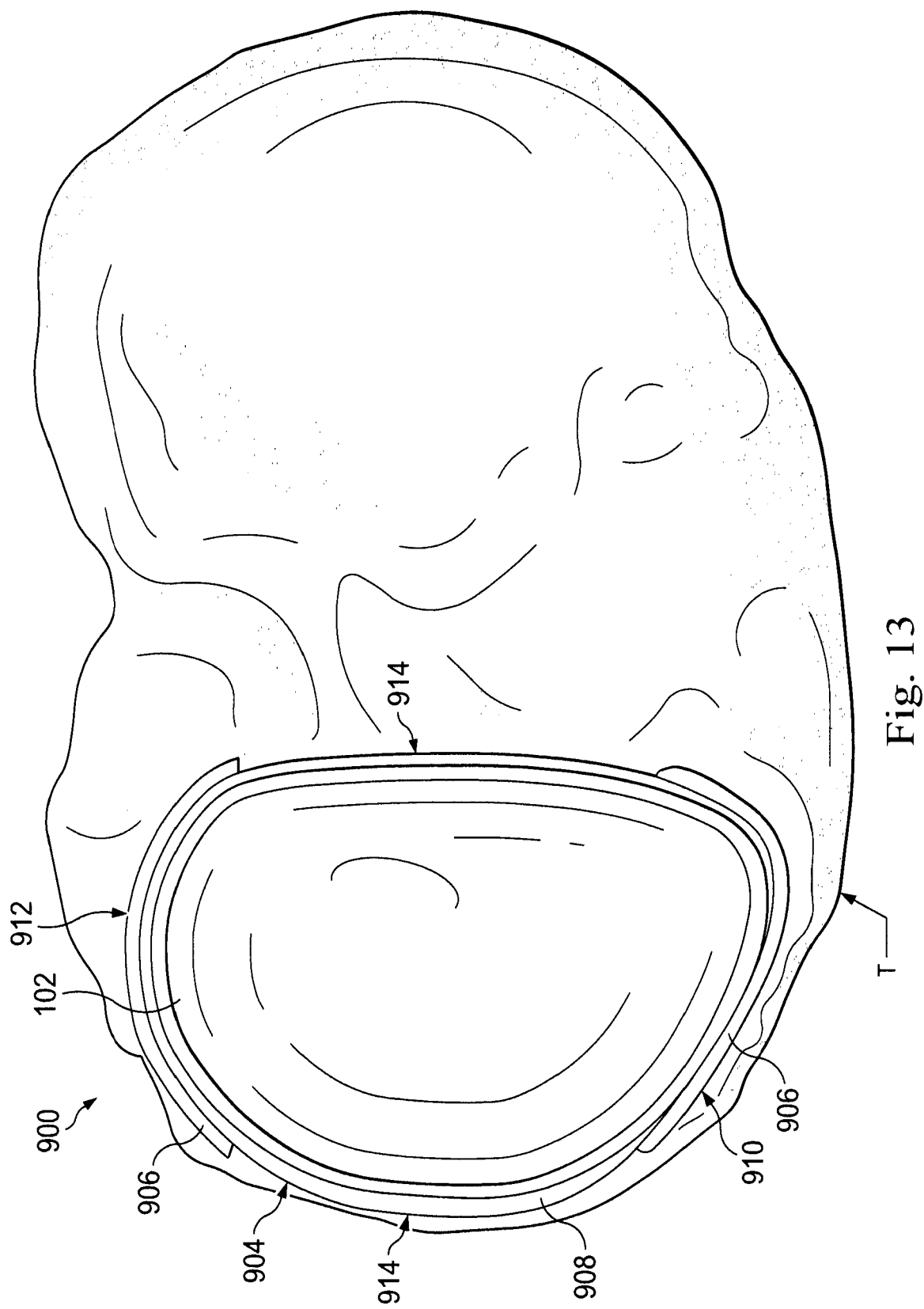
FIG. 13 is a diagrammatic top view of a free floating meniscus component disposed on a tibia according to an exemplary implementation.

FIGS. 12 and 13 show an additional implementation of a prosthetic meniscus device, referenced herein by the numeral 900, disposed on a Tibia T. The prosthetic meniscus device 900 includes the free floating meniscus component 102 and a rigid base component 904. The free floating meniscus component 102 may be similar to those described herein, and those descriptions will not be repeated here. The rigid base component 904 may include an outer portion 906 and a bottom portion 908, together forming a basin or opening for receiving the free floating meniscus component 102. The outer portion 906 may be an outer wall structure extending about and forming an outer peripheral portion of the rigid base component. Thus, the outer portion 906 forms the containment cavity that limits the allowable translation distance of the free floating meniscus component 102. This implementation differs from other rigid base components described herein because the outer portion 906 extends only partially about the bottom portion 908. The bottom portion 908 may be a supporting floor structure. FIG. 12 shows the prosthetic meniscus device 900 disposed on a tibia for use. The rigid base component 904 may include an anterior portion 910, a posterior portion 912, and lateral side portions 914. In the implementation shown, the outer portion 906 extends about the anterior portion 910 and the posterior portion 912, but the lateral side portions 914 are devoid of the outer portion 906. Accordingly, the free floating meniscus component 102 may translate or rotate within the rigid base component 904. However, the rotation within the rigid base component 904 may be limited by the outer portion 906 which maintains the free floating meniscus component 102 in the rigid base component 904. At the same time, the lateral side portions 914 being devoid of the outer portion 906 may permit natural lubricating fluids to more easily enter the sliding interface between the free floating meniscus component 102 and the rigid base component 904. In some implementations, the lateral side portions 914 include an outer portion, but with the outer portion at the lateral side portions 914 having a height lower than the height of the outer portion 906 that is located at the anterior portion 910 and the posterior portion 912. In some implementations, the outer portion 906 has a different height at the anterior portion 910 than at the posterior portion 912. For example, in some implementations the outer portion 906 at the anterior portion 910 has a height less than a height of the outer portion 906 at the posterior portion 912. Other arrangements are also contemplated. The prosthetic meniscus device 900 may perform in the same manner described with reference to FIGS. 10A-10D.

Figure 14:
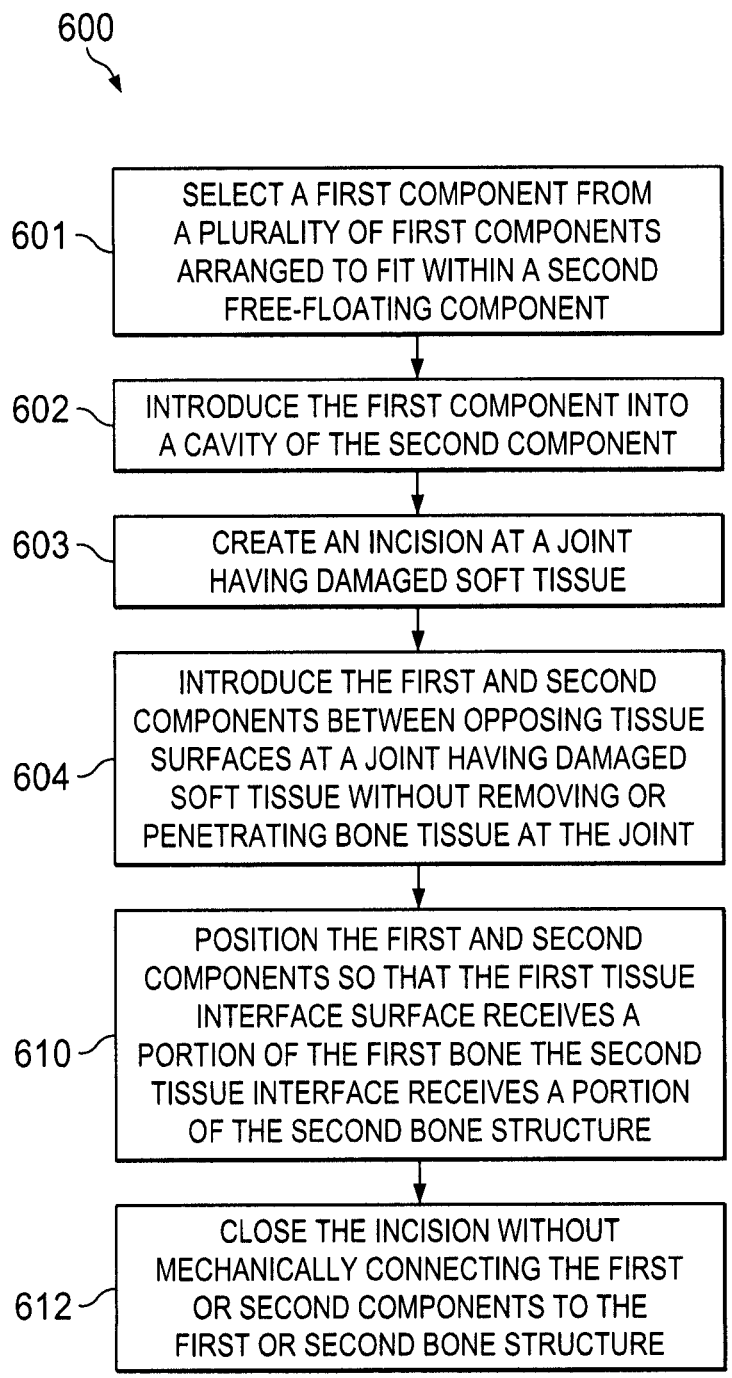
FIG. 14 is a flowchart illustrating an exemplary method of implanting a prosthetic meniscus device in accordance with an exemplary implementation.

FIG. 14 discloses a method 600 of implanting the prosthetic meniscus devices according to an exemplary implementation. The method may be performed, for example, with respect to any of the prosthetic meniscus devices described herein. It is understood that additional steps can be provided before, during, and after the steps of method 600, and that some of the steps described can be replaced or eliminated from the method 600.

In some exemplary implementations, the method begins at 601, with a health care provider assembling the prosthetic meniscus device prior to implantation in a patient. Accordingly, at 601, the health care provider may select a floating meniscus component from a plurality of floating meniscus components arranged to fit within a rigid base component. The floating meniscus component may be any of the floating meniscus components described herein. As described above, in some implementations, a health care provider may be presented with a plurality of floating meniscus components, with each having a particular profile or contour that may match a particular bone structure. In some implementations, the plurality of floating meniscus components may have similar contours, but may be sized differently to match different sized patients.

At 602, the health care provider may introduce the floating meniscus component into a cavity of the rigid base component in a manner permitting the floating meniscus component to translate within the rigid base component.

At 603, the health care provider may create an incision at a joint of a patient having damaged soft tissue in a manner known in the art. At 604, the health care provider may introduce the floating meniscus and rigid base components between opposing tissue surfaces at a joint having damaged soft tissue without removing or penetrating bone tissue at the joint. Accordingly, in some implementations, the health care provider does not carve, cut, or introduce screws, fins, or other anchors into the adjacent bone. As such, the prosthetic meniscus device may be free floating within the joint. That is, it may have the ability to move or slide laterally within the joint, and may have the ability to rotate within the joint. Flexion at the joint may cause the prosthetic meniscus device to translate or rotate. Accordingly, the prosthetic meniscus device is devoid of mechanical anchors and is arranged to interface with the natural tibia plateau and the femoral surface.

At 610, the health care provider may position the floating meniscus and rigid base components so that the first tissue interface surface receives a portion of the first bone the second tissue interface receives a portion of the second bone structure. This may occur when the first tissue-interface surface of the floating meniscus component and the second tissue interface surface of the rigid base component are shaped to fit contours of the adjacent bone structure. In some implementations, this may include a simple concave surface shaped to receive adjacent bone structure. In other implementations, the floating meniscus and rigid base components may be particularly shaped to match a particular bone surface. For example, in some implementations the floating meniscus component is shaped to match the contours of a femoral surface. As such, the first tissue interface surface may receive contours of the femoral bone. Likewise, in some implementations, the rigid base component is shaped to match the contours of a natural tibia plateau. As such, the second tissue interface surface may receive contours of the tibia bone. In other implementations, the tissue interface surfaces may not have specific contours, but may be shaped with concavities or may be relatively planar.

At 612, the health care provider may close the incision without mechanically connecting the floating meniscus or rigid base components to the first or second bone structure. This may enable the prosthetic meniscus device to free float within the joint.

A variety of materials are suitable for use in making components, such as components 102, 104, 852, 854, and 904 of prosthetic devices described herein. In one aspect, the flexible (non-rigid) component forming, such as for example the free floating meniscus component or the softer component is formed from a material that will yield/deform under normal human loading while the rigid material generally does not deform under normal human loading. An example combination may include a flexible component or layer including a material formed from a polycarbonate-urethane having a hardness value of about 3.0 to 9.0 N/mm$^2$ and the rigid material being formed of stainless steel material, or alternatively, a rigid polyurethane, such as COROTHANE polyurethane 75D, having a hardness in the range of about 45 N/mm$^2$ to 85 N/mm$^2$.

Medical grade polyurethane based materials suitable for use in the embodiments described include, but are not limited to, isolated or in combination, the materials described or mentioned in the following paragraphs.

Bionate®, manufactured by DSM, a polycarbonate-urethane is among the most extensively tested biomaterials ever developed. Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability. Bionate® polycarbonate-urethane is a thermoplastic elastomer formed as the reaction product of a hydroxyl terminated polycarbonate, an aromatic diisocyanate, and a low molecular weight glycol used as a chain extender. The results of extensive testing encompassing Histology, Carcinogenicity, Biostability, and Tripartite Biocompatibility Guidance for Medical Devices verifies the cost effective material's biocompatibility.

Another group of suitable materials are copolymers of silicone with polyurethanes as exemplified by PurSil™, a Silicone Polyether Urethane and CarboSil™, a Silicone Polycarbonate Urethane. Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be re-dissolved or re-melted. In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have an excellent flex life, tensile strength exceeding 5000 psi, and ultimate elongations greater than 700 percent. These materials are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, in polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo. DSM synthesized silicone-polyurethane copolymers by combining two previously reported methods: copolymerization of silicone (PSX) together with organic (non-silicone) soft segments into the polymer backbone, and the use of surface-modifying end groups to terminate the copolymer chains.

Other applicable materials include PurSil™ silicone-polyether-urethane and CarboSil™ silicone-polycarbonate-urethane which are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil™) or an aliphatic, hydroxyl-terminated polycarbonate (CarboSil™). The hard segment consists of an aromatic diisocyanate, MDI, with low molecular weight glycol chain extender. The copolymer chains are then terminated with silicone (or other) Surface-Modifying End Groups. Aliphatic (AL) versions of these materials, with a hard segment synthesized from an aliphatic diisocyanate, are also available.

Many of these silicone urethanes demonstrate desirable combinations of physical properties. For example, aromatic silicone polyetherurethanes have a higher modulus at a given shore hardness than conventional polyether urethanes—the higher the silicone content, the higher the modulus (see PurSil™ Properties). Conversely, the aliphatic silicone polyetherurethanes have a very low modulus and a high ultimate elongation typical of silicone homopolymers or even natural rubber (see PurSil™ AL Properties). These properties make these materials very attractive as high-performance substitutes for conventional cross-linked silicone rubber. In both the PTMO and PC families, some polymers have tensile strengths three to five times higher than conventional silicone biomaterials.

Further examples of suitable materials include Surface Modifying End Groups (SMEs) which are surface-active oligomers covalently bonded to the base polymer during synthesis. SMEs—which include silicone (S), sulfonate (SO), fluorocarbon (F), polyethylene oxide (P), and hydrocarbon (H) groups—control surface chemistry without compromising the bulk properties of the polymer. The result is that key surface properties, such as thromboresistance, biostability, and abrasion resistance, are permanently enhanced without additional post-fabrication treatments or topical coatings. This technology is applied to a wide range of DSM's polymers.

SMEs provide a series of base polymers that can achieve a desired surface chemistry without the use of additives. Polyurethanes prepared according to DSM's development process couple endgroups to the backbone polymer during synthesis via a terminal isocyanate group, not a hard segment. The added mobility of endgroups relative to the backbone facilitates the formation of uniform overlayers by the surface-active end blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymers amphipathic characteristics in which the hydrophobic versus hydrophilic balance may be easily controlled.

Other suitable materials, manufactured by CARDIO-TECH CTE, include ChronoFlex® and Hydrothane™.

The ChronoFlex®, polycarbonate aromatic polyurethanes, family of medical-grade segmented biodurable polyurethane elastomers have been specifically developed by CardioTech International to overcome the in vivo formation of stress-induced microfissures.

HydroThane™, hydrophilic thermoplastic polyurethanes, is a family of super-absorbent, thermoplastic, polyurethane hydrogels ranging in water content from 5 to 25% by weight. HydroThane™ is offered as a clear resin in durometer hardness of 80A and 93 Shore A. The outstanding characteristic of this family of materials is the ability to rapidly absorb water, high tensile strength, and high elongation. The result is a polymer having some lubricious characteristics, as well as being inherently bacterial resistant due to their exceptionally high water content at the surface. HydroThane™ hydrophilic polyurethane resins are thermoplastic hydrogels, and can be extruded or molded by conventional means. Traditional hydrogels on the other hand are thermosets and difficult to process.

Additional suitable materials manufactured by THERMEDICS include Tecothane® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane). Tecothane® is a family of aromatic, polyether-based TPU's available over a wide range of durometers, colors, and radiopacifiers. One can expect Tecothane® resins to exhibit improved solvent resistance and biostability when compared with Tecoflex® resins of equal durometers. Carbothane® is a family of aliphatic, polycarbonate-based TPU's available over a wide range of durometers, colors and radiopacifiers. This type of TPU has been reported to exhibit excellent oxidative stability, a property which may equate to excellent long-term biostability. This family, like Tecoflex®, is easy to process and does not yellow upon aging. Tecophilic® is a family of aliphatic, polyether-based TPU's which have been specially formulated to absorb equilibrium water contents of up to 150% of the weight of dry resin.

Additional materials of interest include Tecogel™, a new member to the Tecophilic® family, a hydrogel that can be formulated to absorb equilibrium water contents between 500% to 2000% of the weight of dry resin, and Tecoplast®, a family of aromatic, polyether-based TPU's formulated to produce rugged injection molded components exhibiting high durometers and heat deflection temperatures.

Additional potentially suitable materials include four families of polyurethanes, named Elast-Eon™, which are available from AorTech Biomaterials. In some implementations, the free floating meniscus component may be formed of polyether ether ketone (PEEK), polyetherketoneketone (PEKK), polyethylene, and other polymers.

Elast-Eon™ 1, a Polyhexamethylene oxide (PFMO), aromatic polyurethane, is an improvement on conventional polyurethane in that it has a reduced number of the susceptible chemical groups. Elast-Eon™ 2, a Siloxane based macrodiol, aromatic polyurethane, incorporates siloxane unto the soft segment. Elast-Eon™ 3, a Siloxane based macrodiol, modified hard segment, aromatic polyurethane, is a variation of Elast-Eon™ 2 with further enhanced flexibility due to incorporation of siloxane into the hard segment. Elast-Eon™ 4 is a modified aromatic hard segment polyurethane.

Bayer Corporation also produces candidate materials. Texin® 4210 and Texin® 4215 are thermoplastic polyurethane/polycarbonate blends for injection molding and extrusion. Texin® 5250, 5286 and 5290 are aromatic polyether-based medical grade materials with Shore D hardness of approximately 50, 86, and 90 respectively for injection molding and extrusion.

In some embodiments, the flexible (non-rigid) components of the prosthetic devices are a melt mold composite implant composed of two biocompatible materials: DSM Bionate® Polycarbonate-Urethane (PCU), 80 Shore A, matrix material and ultra high molecular weight polyethylene (UHMWPE) reinforcement material (Dyneema Purity®). In some particular embodiments, a component of prosthetic device formed of PCU and reinforced circumferentially with DSM Dyneema® fibers results in a desirable distribution of loads on the underlying articulation surfaces of the components of the prosthetic device.

Although described in the context of a knee system, the prosthetic devices 100, 850, and 900 described above may be utilized for forming a variety of prosthetic devices. For example, in some instances the composite implants are utilized for knee joints (including meniscus and total knee joints), hip joints (including acetabular cups), shoulder joints, elbow joints, finger joints, and other load and/or non-load receiving prosthetic devices.

In some implementations, the free floating meniscus component and the rigid base component may be formed with a gradient between the soft and hard elements. This gradient may be achieved, in some implementations, using 3-D printing for manufacturing. That is, by 3-D printing one or both of the free floating meniscus component and the rigid base component, a hardness gradient may be generated.

It should be appreciated that in some instances the prosthetic meniscus devices 100, 850, and 900 of the disclosure may be formed by other processes than those described herein. These manufacturing processes include any suitable manufacturing method. For example, without limitation any of the following manufacturing methods may be utilized: injection molding including inserting inserts; compression molding including inserting inserts; injection-compression molding including inserting inserts; compression molding of prefabricated elements pre-formed by any of the above methods including inserting inserts; spraying including inserting inserts; dipping including inserting inserts; machining from stocks or rods; machining from prefabricated elements including inserting inserts; and/or any of the above methods without inserts. Further, it should be appreciated that in some embodiments the prosthetic devices of the disclosure are formed of medical grade materials other than those specifically identified above. In that regard, in some embodiments the prosthetic devices are formed of any suitable medical grade material.

While the principles of the disclosure have been set forth using the specific embodiments discussed above, no limitations should be implied thereby. Any and all alterations or modifications to the described devices, instruments, and/or methods, as well as any further application of the principles of the disclosure that would be apparent to one skilled in the art are encompassed by the disclosure even if not explicitly discussed herein. It is also recognized that various unforeseen or unanticipated alternatives, modifications, and variations of the disclosure may be subsequently made by those skilled in the art. All such variations, modifications, and improvements that would be apparent to one skilled in the art to which the disclosure relates are encompassed by the following claims.

What is claimed is:

1. A two-part joint replacement device for replacing damaged soft joint tissue, the device comprising:
    a free floating soft joint tissue replacement component comprising a first tissue-interface surface shaped to engage a first anatomical structure of a joint having a damaged soft tissue;
    a free floating rigid base component comprising a second tissue-interface surface shaped to engage a second anatomical structure of the joint, the free floating soft joint tissue replacement component being shaped to slidably and rotatably interface with the rigid base component; and
    a space between an outer portion of the free floating soft joint tissue replacement component and an outer portion of the rigid base component, wherein the space allows the free floating soft joint tissue replacement component to float within the rigid base component when the joint is mobile.

2. The two-part joint replacement device of claim 1, wherein the free floating soft joint tissue replacement component comprises an outer surface configured to slidably engage the first anatomical structure, and the rigid base component has an outer surface configured to slidably engage the second anatomical structure.

3. The two-part joint replacement device of claim 1,
    wherein the rigid base comprises a bottom surface,
    wherein the outer portion of the rigid base component comprises an outer wall structure,
    wherein the outer wall structure and the bottom surface form a cavity sized to receive the free floating soft joint tissue replacement component therein, such that the free floating soft joint tissue replacement component floats inside the rigid base, and the rigid base floats inside the joint, and
    wherein the cavity comprises the space between the outer portion of the free floating soft joint tissue replacement component and the outer portion of the rigid base component.

4. The two-part joint replacement device of claim 1, wherein the free floating soft joint tissue replacement component further comprises a bone-relief recess formed on the first tissue-interface surface, wherein the bone-relief recess prevents load-bearing contact between the free floating soft joint tissue replacement component and a portion of the first anatomical structure while the first tissue-interface surface contacts other portions of the first anatomical structure.

5. The two-part joint replacement device of claim 1, wherein the first tissue-interface surface of the free floating soft joint tissue replacement component is formed to fit a shape of a femoral surface.

6. The two-part joint replacement device of claim 1, where an outer surface of a bottom portion of the rigid base component is molded to fit a shape of a natural tibia plateau.

7. The two-part joint replacement device of claim 1, wherein the free floating soft joint tissue replacement component has a concave curvature.

8. The two-part joint replacement device of claim 1, wherein the outer portion of the free floating soft joint tissue replacement component protrudes above a wall structure of the rigid base component.

9. The two-part joint replacement device of claim 1, wherein the free floating soft joint tissue replacement component comprises a polycarbonate-urethane and the rigid base component comprises a bio-compatible metal.

10. The two-part joint replacement device of claim 1, wherein the outer portion of the rigid base component prevents the free floating soft joint tissue replacement component from being expelled from the joint.

11. A method for inserting a two-part joint replacement device inside a joint between a first anatomical structure and an adjacent second anatomical structure, the method comprising:
    introducing a free floating soft joint tissue replacement component and a free floating rigid base component between the first anatomical structure and the second anatomical structure of the joint, wherein the free floating rigid base component is sized to define a space between an outer portion of the free floating soft joint tissue replacement component and an outer portion of the free floating rigid base component, wherein the free floating soft joint tissue replacement component is disposed within the space to slidingly and rotatably engage inside the free floating rigid base component;
    positioning an upper surface of the free floating soft joint tissue replacement component to engage the first bone structure; and
    positioning a bottom portion of the free floating rigid base component to engage the second anatomical structure, such that the two-part joint replacement device floats between the first and second anatomical structures.

12. The method of claim 11, further comprising:
    positioning a bone-relief recess area formed on the upper surface of the free floating soft joint tissue replacement component over a portion of the first anatomical structure to prevent contact between the portion of the first anatomical structure and the joint replacement device.

13. The method of claim 11, wherein the upper surface of the free floating soft joint tissue replacement component is molded to fit a shape of a medial femoral condyle.

14. The method of claim 11, where an outer surface of the bottom portion of the free floating rigid base component is molded to fit a shape of a natural tibia plateau.

15. The method of claim 11, wherein the free floating soft joint tissue replacement component has a concave curvature that fits a shape of a femoral surface.

16. The method of claim 11, further comprising:
    positioning the free floating soft joint tissue replacement component such that an outer portion of the free floating soft joint tissue replacement component protrudes above an outer portion of the free floating rigid base component.

17. The method of claim 11, wherein the free floating soft joint tissue replacement component comprises a polycarbonate-urethane and the free floating rigid base component comprises a bio-compatible metal.

18. A two-part floating joint replacement prosthetic device for replacing damaged soft joint tissue, the prosthetic device comprising:
a free floating first soft joint tissue replacement component comprising an outer perimeter and a first surface for engagement with first anatomical structure having damaged soft joint tissue, the first soft joint tissue replacement component being formed of a first biocompatible material; and
a rigid base second component comprising:
a superiorly extending peripheral wall having an inner surface shaped to receive the outer perimeter of the first soft joint tissue replacement component, wherein the peripheral wall is sized to define a space between the outer perimeter and the inner surface such that the first soft joint tissue replacement component floats in the space; and
a bottom portion arranged to provide free floating engagement with a second anatomical structure,
wherein the rigid base second component is formed of a second biocompatible material more rigid than the first biocompatible material and disposed for direct engagement with bone tissue.

19. The two-part floating joint replacement prosthetic device of claim 18, wherein the first soft joint tissue replacement component further comprises a bone-relief recess formed on an upper surface and prevents contact between the first soft joint tissue replacement component and a portion of a femoral surface.

20. The two-part floating joint replacement prosthetic device of claim 18, wherein an upper surface of the first soft joint tissue replacement component is molded to a shape of a femoral surface.

21. The two-part floating joint replacement prosthetic device of claim 18, where an outer surface of the bottom portion of the rigid base second component is molded to a shape of a natural tibia plateau.

22. The two-part joint replacement device of claim 1,
wherein the first anatomical structure comprises at least one of first bone or first cartilage such that the first tissue-interface surface is shaped to engage at least one of the first bone or the first cartilage,
wherein the second anatomical structure comprises at least one of second bone or second cartilage such that the second tissue-interface surface is shaped to engage at least one of the second bone or the second cartilage.

* * * * *